US009937246B2

(12) United States Patent
Schuchman

(10) Patent No.: US 9,937,246 B2
(45) Date of Patent: Apr. 10, 2018

(54) THERAPEUTIC ACID CERAMIDASE COMPOSITIONS AND METHODS OF MAKING AND USING THEM

(71) Applicant: ICAHN SCHOOL OF MEDICINE AT MOUNT SINAI, New York, NY (US)

(72) Inventor: Edward H. Schuchman, Haworth, NJ (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/776,442

(22) PCT Filed: Mar. 13, 2014

(86) PCT No.: PCT/US2014/026481
§ 371 (c)(1),
(2) Date: Sep. 14, 2015

(87) PCT Pub. No.: WO2014/160390
PCT Pub. Date: Oct. 2, 2014

(65) Prior Publication Data
US 2016/0038574 A1 Feb. 11, 2016

Related U.S. Application Data

(60) Provisional application No. 61/784,594, filed on Mar. 14, 2013.

(51) Int. Cl.
| A61K 38/50 | (2006.01) |
| A61K 38/43 | (2006.01) |
| A61K 38/46 | (2006.01) |
| C12N 9/80  | (2006.01) |
| A61K 45/06 | (2006.01) |

(52) U.S. Cl.
CPC .............. *A61K 38/50* (2013.01); *A61K 38/43* (2013.01); *A61K 38/46* (2013.01); *A61K 45/06* (2013.01); *C12N 9/80* (2013.01); *C12Y 305/01023* (2013.01)

(58) Field of Classification Search
None
See application file for complete search history.

(56) References Cited

U.S. PATENT DOCUMENTS

| 3,966,555 A | 6/1976 | Arnaud et al. |
| 3,972,777 A | 8/1976 | Yamada et al. |
| 4,450,238 A | 5/1984 | Vitobello et al. |
| 4,837,028 A | 6/1989 | Allen |
| 5,019,369 A | 5/1991 | Presant et al. |
| 5,382,524 A | 1/1995 | Desnick et al. |
| 5,401,650 A | 3/1995 | Desnick et al. |
| 5,433,946 A | 7/1995 | Allen, Jr. et al. |
| 5,580,757 A | 12/1996 | Desnick et al. |
| 5,688,766 A | 11/1997 | Revis |
| 6,066,626 A | 5/2000 | Yew et al. |
| 6,258,581 B1 | 7/2001 | Okino et al. |
| 6,350,768 B1 | 2/2002 | Bohme et al. |
| 6,489,117 B2 | 12/2002 | Okino et al. |
| 6,537,785 B1 | 3/2003 | Canfield |
| 6,541,218 B1 | 4/2003 | Schuchman et al. |
| 6,730,297 B1 | 5/2004 | Davidson et al. |
| 6,767,741 B1 | 7/2004 | Epstein et al. |
| RE38,689 E | 1/2005 | Okino et al. |
| 6,858,383 B2 | 2/2005 | Sabbadini |
| 6,881,546 B2 | 4/2005 | Sabbadini |

(Continued)

FOREIGN PATENT DOCUMENTS

| CN | 1688316 A | 10/2005 |
| CN | 101479288 A | 7/2009 |

(Continued)

OTHER PUBLICATIONS

Becker KA et al. Acid Sphingomyelinase Inhibitors Normalize Pulmonary Ceramide and Inflammation in Cystic Fibrosis. 2010. American Journal of Respiratory Cell and Molecular Biology. vol. 42. p. 716-724.*

He X et al. Purification and Characterization of Recombinant, Human Acid Ceramidase. 2003. The Journal of Biological Chemistry. vol. 278, No. 35. pp. 32978-32986.*

Supplementary European Search Report and European Search Opinion for European Application 14775400.6 (dated Jun. 27, 2016).

English Translation and Office Action for Chinese Application No. 201280037341.5 (dated Jul. 26, 2016).

(Continued)

*Primary Examiner* — Paul J Holland
(74) *Attorney, Agent, or Firm* — LeClairRyan, a Professional Corporation

(57) ABSTRACT

The present invention relates to a therapeutic composition including a ceramidase mixture and a pharmaceutically acceptable carrier, where the ceramidase mixture includes an inactive acid ceramidase precursor and an active acid ceramidase. The invention also relates to a method of acid ceramidase treatment, including formulating the acid ceramidase used in said treatment as a ceramidase mixture, where the ceramidase mixture includes an inactive acid ceramidase precursor and an active acid ceramidase. The invention further relates to a method of producing a therapeutic composition including providing a medium containing an inactive acid ceramidase precursor; incubating the medium under conditions effective to transform a portion of the inactive acid ceramidase precursor to active acid ceramidase; and recovering the incubated medium as a ceramidase mixture comprising the inactive acid ceramidase precursor and an active acid ceramidase. The present invention also relates to preparation of a therapeutic composition of a ceramidase lacking acid sphingomyelinase.

15 Claims, 4 Drawing Sheets

(56) References Cited

U.S. PATENT DOCUMENTS

| | | |
|---|---|---|
| 6,884,435 B1 | 4/2005 | O'Hagan et al. |
| 7,018,628 B1 | 3/2006 | Sarkis et al. |
| 7,232,670 B2 | 6/2007 | D'Azzo et al. |
| 7,273,756 B2 | 9/2007 | Adkisson et al. |
| 7,927,587 B2 | 4/2011 | Blazer et al. |
| 8,017,394 B2 | 9/2011 | Adkisson, IV et al. |
| 2003/0087868 A1 | 5/2003 | Yew et al. |
| 2003/0157086 A1 | 8/2003 | Tilly et al. |
| 2003/0211604 A1 | 11/2003 | Brown |
| 2003/0215435 A1 | 11/2003 | Berent |
| 2004/0029779 A1 | 2/2004 | Zhu et al. |
| 2004/0039046 A1 | 2/2004 | Deigner |
| 2004/0172665 A1 | 9/2004 | Reuser et al. |
| 2004/0204379 A1 | 10/2004 | Cheng et al. |
| 2004/0242539 A1 | 12/2004 | Fan et al. |
| 2004/0247603 A1 | 12/2004 | Sabbadini |
| 2004/0248262 A1 | 12/2004 | Koeberl et al. |
| 2005/0026823 A1 | 2/2005 | Zankel et al. |
| 2005/0112640 A1 | 5/2005 | Davidson et al. |
| 2006/0154252 A1 | 7/2006 | Marguerie et al. |
| 2007/0009500 A1 | 1/2007 | Blazar et al. |
| 2007/0162992 A1 | 7/2007 | Burns |
| 2007/0184439 A1 | 8/2007 | Guilford et al. |
| 2007/0292949 A1 | 12/2007 | Duguay et al. |
| 2008/0045470 A1 | 2/2008 | Bielawska et al. |
| 2008/0057590 A1 | 3/2008 | Urdea et al. |
| 2008/0199450 A1 | 8/2008 | Schuchman et al. |
| 2008/0248481 A1 | 10/2008 | Rapko et al. |
| 2008/0292618 A1 | 11/2008 | Weisbart |
| 2010/0068302 A1 | 3/2010 | Ramirez De Molina et al. |
| 2010/0160253 A1 | 6/2010 | Coombe et al. |
| 2010/0285139 A1 | 11/2010 | Gulbins |
| 2011/0091439 A1 | 4/2011 | Bernard et al. |
| 2011/0091442 A1 | 4/2011 | Boyd et al. |
| 2014/0287015 A1 | 9/2014 | Schuchman et al. |
| 2015/0132368 A1 | 5/2015 | Muro Galindo et al. |

FOREIGN PATENT DOCUMENTS

| | | | |
|---|---|---|---|
| CN | 102368905 A | 3/2012 | |
| JP | 2002/542195 A | 12/2002 | |
| JP | 2003/516122 A | 5/2003 | |
| JP | 2004/083465 A | 3/2004 | |
| WO | WO 90/11353 | 10/1990 | |
| WO | WO 00/62780 | 10/2000 | |
| WO | WO 01/26678 A1 | 4/2001 | |
| WO | WO 02/087510 A2 | 11/2002 | |
| WO | WO 2004/057031 A2 | 7/2004 | |
| WO | WO 2006/007560 A2 | 1/2006 | |
| WO | WO 2006/113289 A2 | 10/2006 | |
| WO | WO 2007/089734 A2 | 8/2007 | |
| WO | WO 2007/095688 A1 | 8/2007 | |
| WO | WO 2007/117996 A2 | 10/2007 | |
| WO | WO 2007/136635 A1 | 11/2007 | |
| WO | 2008/086296 A2 | 7/2008 | |
| WO | 2008148063 A1 | 12/2008 | |
| WO | WO 2008/086296 * | 12/2008 | ........... C12N 5/0018 |
| WO | 2009155936 A1 | 12/2009 | |
| WO | WO 2010/127355 A1 | 11/2010 | |
| WO | 2011/025996 A2 | 3/2011 | |
| WO | 2011066352 A1 | 6/2011 | |
| WO | WO 2012/051415 A2 | 4/2012 | |
| WO | 2012/154794 A2 | 11/2012 | |
| WO | WO 2012/177778 A1 | 12/2012 | |
| WO | 2013/036875 A1 | 3/2013 | |
| WO | WO 2013/101276 A2 | 7/2013 | |
| WO | WO 2013/181530 A1 | 12/2013 | |

OTHER PUBLICATIONS

Shtraizent et al., "Autoproteolytic Cleavage and Activation of Human Acid Ceramidase," J. Biol. Chem. 283 (17):11253-11259 (2008).

Simonaro et al., "Acid Ceramidase Improves the Chondrogenic Phenotype of Primary and Mesenchymal Stem Cell Derived Chondrocytes: Implications for Cartilage Repair," Osteoarthritis and Cartilage 19(S1):S114-S115 (2011).

Ramsubir et al., "In Vivo Delivery of Human Acid Ceramidase Via Cord Blood Transplantation and Direct Injection of Lentivirus as Novel Treatment Approaches for Farber Disease," Mol. Genet. Metab. 95(3):133-141 (2008).

Huang et al., "Elevation of the Level and Activity of Acid Ceramidase in Alzheimer's Disease Brain," Europ. J. Neurosci. 20:3489-3497 (2004).

Teichgraber et al., "Ceramide Accumulation Mediates Inflammation, Cell Death and Infection Susceptibility in Cystic Fibrosis," Nat. Med. 14(4):382-391 (2008).

He et al., "Purification and Characterization of Recombinant, Human Acid Ceramidase: Catalytic Reactions and Interactions With Acid Sphingomyelinase," J. Biol. Chem. 278(35):32978-32986 (2003).

Simonaro et al., "Acid Ceramidase Maintains the Chondrogenic Phenotype of Expanded Primary Chondrocytes and Improves the Chondrogenic Differentiation of Bone Marrow-Derived Mesenchymal Stem Cells," PLOS One 8(4): e62715 (2013).

Park et al., "Acid Ceramidase and Human Disease," Biochim. Biophys. Acta 1758:2133-2138 (2006).

International Search Report and Written Opinion for corresponding International Application No. PCT/US2014/026481 (dated Aug. 11, 2014).

Cameron, E.R., "Recent Advances in Transgenic Technology," Molecular Biotechnol. 7:253-265 (1997).

Couzin et al., "As Gelsinger Case Ends, Gene Therapy Suffers Another Blow," Science 307:1028 (2005).

Donsante et al., "AAV Vector Integration Sites in Mouse Hepatocellular Carcinoma," Science 317:477 (2007).

Juengst, E.T., "What Next for Human Gene Therapy?," BMJ 326:1410-11 (2003).

Kappel et al., "Regulating Gene Expression in Transgenic Animals," Current Opinion in Biotechnology 3:548-53 (1992).

Kimmelman, J., "Recent Developments in Gene Transfer: Risk and Ethics," BMJ 350:79-82 (2005).

Mullins et al., "Transgenesis in Nonmurine Species," Hypertension 22(4):630-3 (1993).

Mullins et al., "Transgenesis in the Rat and Larger Mammals," J. Clin. Invest. 97(7):1557-60 (1996).

Raper, S.E., "Gene Therapy: The Good, the Bad, and the Ugly," Surgery 137(5):487-92 (2005).

Rosenberg et al., "Gene Therapist, Heal Thyself," Science 287:1751 (2000).

Touchette, N., "Gene Therapy: Not Ready for Prime Time," Nature Medicine 2(1):7-8 (1996).

Wigley et al., "Site-Specific Transgene Insertion: An Approach," Reprod. Fertil. Dev. 6:585-8 (1994).

Wolff, J.A., "The 'Grand' Problem of Synthetic Delivery," Nat. Biotechnol. 20:768-9 (2002).

Office Action for U.S. Appl. No. 14/516,231 (dated Jun. 22, 2016).

Achord et al., "Human beta-Glucuronidase: In Vivo Clearance and In vitro Uptake by a Glycoprotein Recognition System on Reticuloendothelial Cells," Cell 15(1):269-78 (1978).

Agnieszka et al., "Prenatal Diagnosis-Principles of Diagnostic Procedures and Genetic Counseling," Folia Histochemica et Cytobiologica 45:11-16 (2007).

Almenar-Queralt et al., "Apical Topography and Modulation of ICAM-1 Expression on Activated Endothelium," Am. J. Pathol. 147(5): 1278-88 (1995).

Auclair et al., "Intra-Articular Enzyme Administration for Joint Disease in Feline Mucopolysaccharidosis VI: Enzyme Dose and Interval," Pediatr. Res. 59(4):538-43 (2006).

Barton et al., "Therapeutic Response to Intravenous Infusions of Glucocerebrosidase in a Patient with Gaucher Disease," Proc. Natl. Acad. Sci. USA 87(5): 1913-6 (1990).

Bawab et al., "Ceramidases in the Regulation of Ceramide Levels and Function," Subcellular Biochemistry, vol. 36, Chapter 10, Phospholipid Metabolism in Apoptosis, Quinn et al., Eds., Kluwer Academic/Plenum Publishers, New York (2002).

(56) References Cited

OTHER PUBLICATIONS

Bazian, "Ultra Drug Orphan Drugs for Lysosomal Storage Disorders: A Guideline Comparison and Survey of International Current Practice," 1-70 (2009).
Becker et al., "Acid Sphingomyelinase Inhibitors Normalize Pulmonary Ceramide and Inflammation in Cystic Fibrosis," *Am. J. Respir. Cell Mol. Biol.* 42:716-24 (2010).
Berlin and Oliver, "Surface Functions During Mitosis," *J. Cell. Biol.* 85:660-671 (1980).
Bernardo et al., "Purification, Characterization, and Biosynthesis of Human Acid Ceramidase," *J. Biol. Chem.* 270(19): 11098-11102 (1995).
Bernstein et al., "Fabry Disease: Six Gene Rearrangements and an Exonic Point Mutation in the alpha-Galactosidase Gene," *J. Clin. Invest.* 83(4):1390-1399 (1989).
Beutler et al., "Purification and Properties of Human alpha-Galactosidases," *J.Biol. Chem.* 247(22):7195-7200 (1972).
Beutler, E., "Gaucher Disease: New Molecular Approaches to Diagnosis and Treatment," *Science* 256:794-799 (1992).
Bhowmick et al., "Effect of Flow on Endothelial Endocytosis of Nanocarriers Targeted to ICAM-1," *J. Controlled Release* 157(3):485-492 (2012).
Bielicki et al., "Advantages of Using Same Species Enzyme for Replacement Therapy in a Feline Model of Mucopolysaccharidosis Type VI," *The Journal of Biological Chemistry* 274(51):36335-36343 (1999).
Bielicki et al., "Recombinant Canine alpha-L-Fucosidase: Expression, Purification, and Characterization," *Mol. Gen. Metabolism* 69:24-32 (2000).
Bishop et al., "Affinity Purification of alpha-Galactosidase A From Human Spleen, Placenta, and Plasma With Elimination of Pyrogen Contamination. Properties of the Purified Splenic Enzyme Compared to other Forms," *J. Biol. Chem.* 256(3):1307-1316 (1981).
Bishop et al., "Enzyme Therapy XX: Further Evidence for the Differential In Vivo Fate of Human Splenic and Plasma . . . ", in *Lysosomes and Lysosomal Storage Diseases*, Eds. Callahan et al. Raven Press; 381-94 (1981).
Bishop et al., "Human alpha-Galactosidase A: Nucleotide Sequence of a cDNA Clone Encoding the Mature Enzyme," *Proc. Natl. Acad. Sci.* 83(13):4859-4863 (1986).
Bishop et al., "Human α-Galactosidase: Characterization and Eukaryotic Expression of the Full-Length cDNA and Structural Organization of the Gene" in *Lipid Storage Disorders*, Eds. Salvayre et al. Plenum Publishing Corp 809-822 (1988).
Bishop et al., "Molecular Cloning and Nucleotide Sequencing of a Complementary DNA Encoding Human Alpha Galactosidase A," *Am. J. Hum. Genetics* 37 (4 Suppl):A144 (1985).
Bishop et al., "Purification and Characterization of Human alpha-Galactosidase Isozymes: Comparison of Tissue and Plasma Forms and Evaluation of Purification Methods," *Birth Defects Original Article Series*; XVI(1): 17-32 (1980).
Bishop et al., "Structural Organization of the Human alpha-Galactosidase A Gene: Further Evidence for the Absence of a 3' Untranslated Region," *Proc. Natl. Acad. Sci.* 85(11):3903-3907 (1988).
Bodas et al., "Critical Modifier Role of Membrane-Cystic Fibrosis Transmembrane Conductance Regulator-Dependent Ceramide Signaling in Lung Injury and Emphysema," *J. Immunol.* 186:602-613 (2011).
Bonten et al., "Targeting Macrophages With Baculovirus-Produced Lysosomal Enzymes: Implications for Enzyme Replacement Therapy of the Glycoprotein Storage Disorder Galactosialidosis," *FASEB J.* 18(9):971-3 (Epub 2004).
Boose et al., "Conditional Intercellular Cohesion in a *Dictyostelium discoideum* Mutant Which is Temperature Sensitive for Correct Processing of Asparagine-Linked Oligosaccharides," *Glycobiology* 1(3):295-305 (1991).
Brady et al., "Enzyme Replacement Therapy: Conception, Chaos and Culmination." *Phil. Trans. R. Soc. London B Biol. Sci.* 358(1433):915-9 (2003).
Brady et al., "Modifying Exogenous Glucocerebrosidase for Effective Replacement Therapy in Gaucher Disease," *J. Inherit. Dis.* 17(4):510-9 (1994).
Brady et al., "Replacement Therapy for Inherited Enzyme Deficiency. Use of Purified Ceramidetrihexosidase in Fabry's Disease." *N. Engl. J. Med.* 289(1):9-14 (1973).
Broun et al., "Catalytic Plasticity of Fatty Acid Modification Enzymes Underlying Chemical Diversity of Plant Lipids," *Science* 282:1315-1317 (1998).
Cabrera-Salazar et al., "Gene Therapy for the Lysosomal Storage Disorders," *Curr. Opin. Mol. Ther.* 4(4):349-58 (2002).
Calhoun et al., "Fabry Disease: Isolation of a cDNA Clone Encoding Human Alpha-Galactosidase A," *Proc. Natl. Acad. Sci.* 82(21):7364-7368 (1985).
Callahan et al., "Alpha-N-Acetylgalactosaminidase: Isolation, Properties and Distribution of the Human Enzyme," *Biochemical Med.* 7(3):424-431 (1973).
Chavez et al., "Acid Ceramidase Overexpression Prevents the Inhibitory Effects of Saturated Fatty Acids in Insulin Signaling," *J. Biol. Chem.* 280(20):20148-53 (2006).
Chelikani et al., "Diversity of Structures and Properties Among Catalases," *Cell Mol. Life Sci.* 61:192-208 (2004).
Chica et al., "Semi-Rational Approaches to Engineering Enzyme Activity: Combining the Benefits of Directed Evolution and Rational Design," *Curr. Opi. Biotechnol.* 16:378-384 (2005).
Christofidou-Solomidou et al., "Vascular Immunotargeting of Glucose Oxidase to the Endothelial Antigens Induces Distinct Forms of Oxidant Acute Lung Injury: Targeting to Thrombomodulin, but not to PECAM-1, Causes Pulmonary Thrombosis and Neutrophil Transmigration," *Am. J. Pathol.* 160(3):1155-69 (2002).
Conner and Schmid, "Regulated Portals of Entry Into the Cell," *Nature* 422:37-44 (2003).
Coppola et al., "Construction of Baculovirus Derivatives that Overproduce Human α-Galactosidase A," *J. Cell. Biochem. Suppl.* Abstract No. K306 13D:227-347 (1989).
D' Azzo, "Gene Transfer Strategies for Correction of Lysosomal Storage Disorders," *Acta Haematol.* 110(2-3):71-85 (2003).
Daly & Sands, "Gene Therapy for Lysosomal Storage Diseases," *Expert Opin. Invest. Drugs* 7(10):1673-82 (1998).
Dean et al., "Studies on Human Liver Alpha-Galactosidases. II. Purification and Enzymatic Properties of Alpha-Galactosidase B (alpha-N-acetylgalactosaminidase)," *J. Biol. Chem.* 254(20):10001-10005 (1979).
Dean et al., "The Identification of Alpha-Galactosidase B From Human Liver as an Alpha-N-Acetylgalactosaminidase," *Biochem. Biophys. Res. Commun.* 77(4): 1411-1417 (1977).
Desnick et al., "Enzyme Replacement and Enhancement Therapies: Lessons From Lysosomal Disorders," *Nature Rev. Genet.*; 3(12):954-66 (2002).
Desnick et al., "Enzyme Therapy in Fabry Disease: Differential In Vivo Plasma Clearance and Metabolic Effectiveness of Plasma and Splenic Alpha-Galactosidase A Isozymes," *Proc. Natl. Acad. Sci. USA* 76(10):5326-5330 (1979).
Desnick et al., "Enzyme therapy XVII: Metabolic and Immunologic Evaluation of Alpha-Galactosidase A Replacement in Fabry Disease," *Birth Defects Original Article Series*; XVI(1):393-413 (1980).
Desnick et al., "Fabry Disease: a-Galactosidase Deficiency; Schindler Disease: α-N-Acetylgalactosaminidase Deficiency." in *The Metabolic Basis of Inherited Disease*, eds. Scriver et al. McGraw Hill, NY; 70: 1751-96 (1989).
Desnick et al., "Fabry Disease: Molecular Diagnosis of Hemizygotes and Heterozygotes," *Enzyme* 38(1-4):54-64 (1987).
Desnick et al., "Schindler Disease: An Inherited Neuroaxonal Dystrophy Due to alpha-N-Acetylgalactosaminidase Deficiency," *J. Inher. Metab. Dis.* 13:549-559 (1990).
Devos et al., "Practical Limits of Function Prediction," *Proteins: Structure, Function, and Genetics* 41:98-107 (2000).
Dhami et al., "Mannose 6-phosphate Receptor-Mediated Uptake is Defective in Acid Sphingomyelinase-Deficient Macrophages: Implications for Niemann-Pick Disease Enzyme Replacement Therapy," *J. Biol. Chem.* 279(2): 1526-32 (2004).

(56) References Cited

OTHER PUBLICATIONS

Diamond et al., "Binding of the Integrin Mac-1 (CD11b/CD18) to the Third Immunoglobulin-Like Domain of ICAM-1 (CD54) and its Regulation by Glycosylation," *Cell* 65:961-71 (1991).
Eliyahu et al., "Acid Ceramidase Improves the Quality of Oocytes and Embryos and the Outcome of in Vitro Fertilization," *FASEB J.* 24:1229-38 (2010).
Eliyahu et al., "Acid Ceramidase is a Novel Factor Required for Early Embryo Survival," Abstract Presented in Mar. 2007.
Eliyahu et al., "Acid Ceramidase is a Novel Factor Required for Early Embryo Survival," *FASEB J.* 21:1403-09 (May 2007).
Eliyahu et al., "Anti-TNF-Alpha Therapy Enhances the Effects of Enzyme Replacement Therapy in Rats with Mucopolysaccharidosis Type VI," *PLOS ONE* 6(8):e22447 (2011).
Eliyahu et al., "Identification of Cystatin SA as a Novel Inhibitor of Acid Ceramidase," *J. Biol. Chem.* 286(41):35624-33 (2011).
Ellinwood et al., "Gene Therapy for Lysosomal Storage Diseases: The Lessons and Promise of Animal Models," *J. Gene Med.* 6(5):481-506 (2004).
Eng et al., "Safety and Efficacy of Recombinant Human alpha-Galactosidase A Replacement Therapy in Fabry's Disease," *N. Eng. J. Med.* 345(1):9-16 (2001).
Estruch et al., "Non-Viral, Integrin-Mediated Gene Transfer into Fibroblasts From Patients With Lysosomal Storage Diseases." in *J. Gene Med.* 3(5):488-97 (2001).
European Patent Application No. 08727393.4, Supplementary European Search Report (dated Sep. 9, 2010).
European Patent Office Communication and Examination Report for European Patent Application No. 08727393.4 (dated Dec. 4, 2014).
Extended European Search Report and Opinion for European Patent Application No. 12830086.0 (dated Jul. 13, 2015).
Extended European Search Report for European Patent Application No. 12803458.4 (dated Mar. 20, 2015).
Farkas et al., "The Recycling of Apolipoprotein E and its Amino-Terminal 22 kDa Fragment: Evidence of Multiple Redundant Pathways," *J. Lipid Res.* 45:1546-1554 (2004).
Fawcett, "Surface Specializations of Absorbing Cells," *J. Histochem. Cytochem.* 13(2):75-91 (1965).
Ferlinz et al., "Functional Characterization of the N-Glycosylation Sites of Human Acid Sphingomyelinase by Site-Directed Mutagenesis," *Eur. J. Biochem.* 243:511-517 (1997).
Ferlinz et al., "Occurrence of Two Molecular Forms of Human Acid Sphingomyelinase," *Biochem. J.* 301:855-862 (1994).
First Office Action and English Translation for Chinese Patent Application No. 201280037341.5 (dated Dec. 3, 2014).
Fox et al., "Circulating Sphingolipid Biomarkers in Models of Type 1 Diabetes," *Journal of Lipid Research*, 30 pp., retrieved from www.jlr.org on Jan. 6, 2011.
Friedman et al., "A Comparison of the Pharmacological Properties of Carbohydrate Remodeled Recombinant and Placental-Derived beta-Glucocerebrosidase: Implications for Clinical Efficacy in Treatment of Gaucher Disease," *Blood* 93(9):2807-16 (1999).
Furbish et al., "Uptake and Distribution of Placental Glucocerebrosidase in Rat Hepatic Cells and Effects of Sequential Deglycosylation," *Biochem. Biophys. Acta.* 673(4):425-34 (1981).
Gao et al., "Delivery of a Retroviral Vector Expressing Human beta-Glucuronidase to the Liver and Spleen Decreases Lysosomal Storage in Mucopolysaccharidosis VII Mice," *Mol. Ther.* 2(2):233-44 (2000).
Garman & Garboczi, "The Molecular Defect Leading to Fabry Disease: Structure of Human α-Galactosidase", *J. Mol. Biol.* 337(2):319-335 (2004).
Garman et al., "The 1.9 a Structure of α-N-Acetylgalactosaminidase", *Structure* 10(3):425-434 (2002).
Gilbert et al., "Sphingomyelinase Decreases Type II Collagen Expression in Bovine Articular Cartilage Chondrocytes via the ERK Signaling Pathway," *Arthritis & Rheumatism* 58(1):209-220 (2008).

Gole et al. "Plasma Proteins Modified by Tyrosine Nitration in Acute Respiratory Distress Syndrome," *Am. J. Physiol. Lung Cell Mol. Physiol.* 278(5):L961-967 (2000).
Grabowski et al., "Enzyme Therapy for Lysosomal Storage Disease: Principles, Practice, and Prospects." *Aunu. Rev. Genomics Hum. Genet.*; 4:403-36 (2003).
Grabowski et al., "Enzyme Therapy in Type 1 Gaucher Disease: Comparative Efficacy of Mannose-Terminated Glucocerebrosidase from Natural and Recombinant Sources," *Ann. Intern. Med.* 122:33-39 (1995).
Grassme et al., "CTFR-Dependent Susceptibility of the Cystic Fibrosis-Host to Pseudomonas aeruginosa," *Int. J. Med. Microbiol.* 300:578-583 (2010).
Hanzopoulos & Calhoun, "Expression of the Human alpha-Galactosidase A in *Escherichia coli* K-12," *Gene (Amst.)* 57(2-3):159-169 (1987).
Harmatz et al., "Enzyme Replacement Therapy in Mucopolysaccharidosis VI (Maroteaux-Lamy Syndrome)," *J. Pediatr.* 144:574-80 (2004).
Hasholt & Sorenson, "Lysosomal Alpha-Galactosidase in Endothelial Cell Cultures Established From a Fabry Hemizygous and Normal Umbilical Veins," *Human Genet.* 72(1):72-76 (1986).
Haskins et al., "Bone Marrow Transplantation Therapy for Metabolic Disease: Animal Models as Predictors of Success and in Utero Approaches," *Bone Marrow Transplant* 18(Suppl. 3): S25-S27 (1996).
He et al., "Characterization of Human Acid Sphingomyelinase pPurified From the Media of Overexpressing Chinese Hamster Ovary Cells," *Biochim. Biophys. Acta.* 1432(2):251-64 (1999).
He et al., "Deregulation of Sphingolipid Metabolism in Alzheimer's Disease," *Neurobiology of Aging* 31(3):398-408 (2010).
Hers et al., "Alpha-Glucosidase Deficiency in Generalized Glycogenstorage Gisease (Pompe's Gisease)," *Biochem. J.* 86:11-16 (Jan. 1963).
Hlavacek et al., "Steric Effects on Multivalent Ligand-Receptor Binding: Exclusion of Ligand Sites by Bound Cell Surface Receptors," *Biophysical J.* 76:3031-3043 (1999).
Hoogerbrugge et al., "Effect of Bone Marrow Transplantation on Enzyme Levels and Clinical Course in the Neurologically Affected Twitcher Mouse," *J. Clin. Invest.* 81(6): 1790-4 (Jun. 1988).
Huang et al., "A Comparison of the Signal Pathways Between the TNFalpha- and Oridonin-Induced Murine L929 Fibrosarcoma Cell Death," *Acta Med. Okayama* 59(6):261-70 (2005).
International Preliminary Report on Patentability for PCT/US2008/050418 (dated Jul. 16, 2009).
International Search Report and Written Opinion for PCT/US2008/050418 (dated Oct. 8, 2008).
International Search Report and Written Opinion for International Application No. PCT/US05/23529 (dated Aug. 2, 2006).
International Search Report and Written Opinion for PCT Application No. PCT/US2012/043369 (dated Aug. 31, 2012).
International Search Report and Written Opinion for PCT/US10/33422 (dated Jun. 29, 2010).
International Search Report and Written Opinion for PCT/US11/56147 (dated Apr. 26, 2012).
International Search Report and Written Opinion for PCT/US13/043608 (dated Oct. 21, 2013).
International Search Report and Written Opinion for PCT/US2012/031847 (dated Jul. 22, 2013).
International Search Report and Written Opinion for PCT/US2012/054316 (dated Dec. 20, 2012).
Ioannou et al., "Overexpression and Characterization of Human alpha-Galactosidase," in *Inborn Errors of Metabolism, 5th International Congress*, Abstract No. OC4.3, Pacific Grove, CA (Jun. 1-5, 1990).
Ioannou et al., "Fabry Disease: Preclinical Studies Demonstrate the Effectiveness of alpha-Galactosidase A Replacement in Enzyme-Deficient Mice," *Am J. Hum. Genet.* 68:14-25 (2001).
Isemura et al., "Characterization and Amino Acid Sequence of New Acidic Cysteine Proteinase Inhibitor (Cystatin SA) Structurally Closely Related to Cystatin S, From Human Whole Saliva," *J. Biochem.* 102(4):693-704 (1987).

(56) References Cited

OTHER PUBLICATIONS

Jan et al., "Sindbis Virus Entry Into Cells Triggers Apoptosis by Activating Sphingomyelinase,"*J. Virol.* 74(14):6425-32 (2000).
Jin et al., "Ex Vivo Gene Therapy Using Bone Marrow-Derived Cells: Combined Effects of Intracerebral and Intravenous Transplantation in a Mouse Model of Niemann-Pick Disease," *Mol. Ther.* 8(6):876-85 (2003).
Jin et al., "Intracerebral Transplantation of Mesenchymal Stem Cells Into Acid Sphingomyelinase-Deficient Mice Delays the Onset of Neurological Abnormalities and Extends Their Life Span." *J. Clin. Invest.* 109(9):1183-91 (2002).
Kakkis et al., "Long-Term and High-Dose Trials of Enzyme Replacement Therapy in the Canine Model of Mucopolysaccharidosis I," *Biochem. Mol. Med.* 58:156-67.
Kaplan et al., "Phosphohexosyl Components of a Lysosomal Enzyme are Recognized by Pinocytosis Receptors on Human Fibroblasts," *Proc. Natl. Acad. Sci. USA*; 74(5):2026-30 (1977).
Kato et al., "Cystatin SA, A Cysteine Proteinase Inhibitor, Induces Interferon-Gamma Expression in CD4-Positive T Cells," *Biol. Chem.* 385(5):419-22 (2004).
Kishida et al., "Docosahexaenoic Acid Enrichment Can Reduce L929 Cell Necrosis Induced by Tumor Necrosis Factor," *Biochim. Biophys. Acta* 1761:454-62 (2006).
Kisselev, L., "Polypeptide Release Factors in Prokaryotes and Eurkaryotes: Same Function, Different Structure," *Structure* 10:8-9 (2002).
Klabunde et al., "Mechanism of FE(III)-Zn(II) Purple Acid Phosphatase Based on Crystal Structures," *J. Mol. Biol.* 259:737-748 (1996).
Kölzer et al., "Functional Characterization of the Postulated Intramolecular Sphingolipid Activator Protein Domain of Human Acid Sphingomyelinase," *Biol. Chem.* 385:1193-1195 (2004).
Kornfeld et al., "Lysosomal Enzyme Targeting," *Biochem. Soc. Trans.* 18(3):367-74 (1990).
Kornfeld et al., "Trafficking of Lysosomal Enzymes," *FASEB J.* 1(6):462-468 (1987).
Kornfeld et al., "Steps in the Phosphorylation of the High Mannose Oligosaccharides of Lysosomal Enzymes," *CIBA Found. Symp.*; (92):138-56 (1982).
Kornreich et al., "Alpha-Galactosidase A Gene Rearrangements Causing Fabry Disease. Identification of Short Direct Repeats at Breakpoints in an Alu-Rich Gene," *J. Biol. Chem.* 265(16): 9319-9326 (1990).
Kornreich et al., "Nucleotide Sequence of the Human Alpha-Galactosidase A Gene," *Nuc. Acids. Res.* 17(8):3301-3302 (1989).
Kozower et al., "Immunotargeting of Catalase to the Pulmonary Endothelium Alleviates Oxidative Stress and Reduces Acute Lung Transplantation Injury," *Nat. Biotechnol.* 21(4):392-8 (2003).
Krivit et al., "State of the Art Review. Bone Marrow Transplantation Treatment for Storage Diseases.Keystone," *Bone Marrow Transplant* 10(Suppl. 1): 87-96 (1992).
Kusiak et al., "Purification and Properties of the Two Major Isozymes of Alpha-Galactosidase From Human Placenta," *J. Biol. Chem.* 253(1): 184-190 (1978).
Lansmann et al., "Human Acid Sphingomyelinase—Assignment of the Disulfide Bond Pattern," *Eur. J. Biochem.* 270:1076-1088 (2003).
Le Roy et al., "Clathrin-and non-Clathrin Mediated Endocytic Regulation of Cell Signalling," *Nature* 6:112-126 (2005).
Lebowitz et al., "Glycosylation-Independent Targeting Enhances Enzyme Delivery to Lysosomes and Decreases Storage in Mucopolysaccharidosis Type VII Mice," *Proc. Natl. Acad. Sci. USA* 101(9):3083-8 (2004).
Leimig et al., "Functional Amelioration of Murine Galactosialidosis by Genetically Modified Bone Marrow Hematopoietic Progenitor Cells," *Blood* 99(9):3169-78 (2002).
Lemansky et al., "Synthesis and Processing of Alpha-Galactosidase A in Human Fibroblasts. Evidence for Different Mutations in Fabry Disease," *J. Biol. Chem.* 262(5):2062-2065 (1987).
Li et al., "Insertional Mutagenesis of the Mouse Acid Ceramidase Gene Leads to Early Embryonic Lethality in Homozygotes and Progressive Lipid Storage Disease in Heterozygotes," *Genomics* 79(2):218-24 (2002).
Lin et al., "*Caenorhabditis elegans* Contains Two Distinct Acid Sphingomyelinases," *J. Biol. Chem.* 273(23): 14374-14379 (1998).
Liu et al., "Acid Ceramidase Upregulation in Prostate Cancer: Role in Tumor Development and Implications for Therapy," *Expert Opinions in Therapeutic Targets* 13(12):1449-1458 (2009).
Macrae et al., "Ceramide Inhibition of Chondrocyte Proliferation and Bone Growth is IGF-I Independent," *Journal of Endocrinology* 191:369-377 (2006).
Malatack et al., "The Status of Hematopoietic Stem Cell Transplantation in Lysosomal Storage Disease," *Pediatr. Neurol.* 29(5):391-403 (2003).
Mao et al., "Cloning and Characterization of a Novel Human Ceramidase," *J. Biol. Chem.* 276(28):26577-26588 (2001).
Marquass et al., "Matrix-Associated Implantation of Predifferentiated Mesenchymal Stem Cells Versus Articular Chondrocytes, In Vivo Results of Cartilage Repair After 1 Year," *The American Journal of Sports Medicine* 39(7):1401-1412 (2011).
Medline Plus Online Dictionary; Definition for "embryo".
Meikle et al., "Prevalence of Lysosomal Storage Disorders." *JAMA* 281(3): 249-54 (1999).
Mielke et al., "Alterations of the Sphingolipid Pathway in Alzheimer's Disease: New Biomarkers and Treatment Targets?," *Neuromol. Med.* 12:331-340 (2010).
Mintzer et al., "A Novel High-Throughput Screening Format to Identify Inhibitors of Secreted Acid Sphingomyelinase," *J. Biomol. Screen* 10(3):225-34 (2005).
Miranda et al., "Biochemical, Pathological, and Clinical Response to Transplantation of Normal Bone Marrow Cells Into Acid Sphingomyelinase-Deficient Mice," *Transplantation* 65(7):884-92 (1998).
Miranda et al., "Bone Marrow Transplantation in Acid Sphingomyelinase-Deficient Mice: Engraftment and Cell Migration Into the Brain as a Function of Radiation, Age, and Phenotype," *Blood* 90(1):444-52 (1997).
Miranda et al., "Hematopoietic Stem Cell Gene Therapy Leads to Marked Visceral Organ Improvements and a Delayed Onset of Neurological Abnormalities in the Acid Sphingomyelinase Deficient Mouse Model of Niemann-Pick Disease," *Gene Ther.* 7:1768-76 (2000).
Miranda et al., "Infusion of Recombinant Human Acid Sphingomyelinase into Niemann-Pick Disease Mice Leads to Visceral, but Not Neurological, Correction of the Pathophysiology," *FASEB J.* 14:1988-95 (2000).
Mistry et al., "Therapeutic Delivery of Proteins to Macrophages: Implications for Treatment of Gaucher's Disease." *Lancet* 348(9041):1555-9 (1996).
Monick et al., "Cooperative Prosurvival Activity by ERK and AKT in Human Alveolar Macrophages is Dependent on High Levels of Acid Ceramidase Activity," *J. Immunol.* 173:123-35 (2004).
Morita et al., "Oocyte Apoptosis Is Suppressed by Disruption of the Acid Sphingomyelinase Gene or by Sphingosine-1-Phosphate Therapy," *Nat. Med.* 6(10):1109-14 (2000).
Murciano et al., "ICAM-Directed Vascular Immunotargeting of Antithrombotic Agents to the Endothelial Luminal Surface," *Blood* 101(10):3977-84 (2003).
Muro et al., "A Novel Endocytic Pathway Induced by Clustering Endothelial ICAM-1 or PECAM-1." *J. Cell Sci.* 116(Pt 8):1599-609 (2003).
Muro et al., "Endothelial Endocytic Pathways: Gates for Vascular Drug Delivery," *Curr. Vasc. Pharmacol.* 2(3 ):281-99 (2004).
Muro et al., "ICAM-1 Recycling in Endothelial Cells: A Novel Pathway for Sustained Intracellular Delivery and Prolonged Effects of Drugs," *Blood* 105(2):650-8 (2005).
Muro et al., "Slow Intracellular Trafficking of Catalase Nanoparticles Targeted to ICAM-1 Protects Endothelial Cells From Oxidative Stress," *Am. J. Physiol. Cell Physiol.* 285(5):C1339-47 (2003).
Murray, "Lectin-Specific Targeting of Lysosomal Enzymes to Reticuloendothelial Cells," *Meth. Enzymol.* 149:25-42 (1987).

(56) References Cited

OTHER PUBLICATIONS

Naslavsky et al., "Characterization of a Nonclathrin Endocytic Pathway: Membrane Cargo and Lipid Requirements," *Mol. Biol. Cell.* 15:3542-3552 (2004).

Nejadnik et al., "Autologous Bone Marrow-Derived Mesenchymal Stem Cells Versus Autologous Chondrocyte Implantation: An Observational Cohort Study," *The American Journal of Sports Medicine* 38(6):1110-1116 (2010).

Newman et al., "The Biology of PECAM-1," *J. Clin. Invest.* 99(1):3-8 (1997).

Newrzella et al., "Functional Analysis of the Glycosylation of Murine Acid Sphingomyelinase," *J. Biol. Chem.* 271(50):32089-32095 (1996).

Newrzella et al., "Molecular Cloning of the Acid Sphingomyelinase of the Mouse and the Organization and Complete Nucleotide Sequence of the Gene," *Biol. Chem. Hoppe-Seyler* 373:1233-1238 (1992).

Nichols et al., "Endocytosis Without Clathrin Coats," *TRENDS in Cell Biol.* 11(10):406-412 (2001).

Office Action for Canadian Patent Application No. 2,674,849 (dated Feb. 4, 2015).

Okino et al., "The Reverse Activity of Human Acid Ceramidase," *J. Biol. Chem.* 278(32):29948-53 (2003).

Pandey et al., "Recent Advances in the Immunology of Ceramide," *Exp. Mol. Pathol.* 82:298-309 (2007) (E-pub Oct. 12, 2006).

Park et al., "Ceramide, A Crucial Functional Lipid and Its Metabolic Regulation by Acid Ceramidase," *Food Science & Biotechnology* 19(4):859-864 (2010).

Partial Supplementary European Search Report for European Patent Application No. 12830086.0 (dated Mar. 5, 2015).

Partial Supplementary European Search Report for European Patent Application No. 12803458.4 (dated Dec. 1, 2014).

Pasqualotto et al., "Effect of Oxidative Stress in Follicular Fluid on the Outcome of Assisted Reproductive Procedures," *Fertility and Sterility* 81(4):973-76 (2004).

Patrizio et al., "Molecular Methods for Selection of the Ideal Oocyte," *Reproductive BioMedicine Online* 15(3):346-53 (2007).

Perez et al., "A Central Role for Ceramide in the Age-Related Acceleration of Apoptosis in the Female Germline," *FASEB J.* 19(7):860-2 (2005).

Pittis et al., "Acid Sphingomyelinase: Identification of Nine Novel Mutations Among Italian Niemann Pick Type B Patients and Characterization of In Vivo Functional In-Frame Start Codon," *Human Mutation, Mutation in Brief #734* p. 1-7 (2004).

Ponting et al., "Acid sphingomyelinase possesses a domain homologous to its activator proteins: saposins Band D," *Protein Science* 3:359-361 (1994).

Pratico et al., "Localization of Distinct F2-Isoprostanes in Human Atherosclerotic Lesions." *J. Clin. Invest.* 100(8):2028-34 (1997).

Prince et al., "Lipoprotein Receptor Binding, Cellular Uptake, and Lysosomal Delivery of Fusions Between the Receptor-Associated Protein (RAP) and Alpha-L-Iduronidase or Acid Alpha-Glucosidase," *J. Biol. Chem.* 279(33):35037-46 (2004).

Qui et al., "Activation of Human acid Sphingomyelinase Through Modification or Deletion of C-Terminal Cysteine," *J. Biol. Chem.* 278(35):32744-32752 (2003).

Quinn et al., "A Genomic Clone Containing the Promoter for the Gene Encoding the Human Lysosomal Enzyme, Alpha-Galactosidase A," *Gene (Amst.).* 58(2-3): 177-188 (1987).

Quintern et al., "Acid Sphingomyelinase From Human Urine: Purification and Characterization," *Biochimica et Biophysica Acta.* 922:323-336 (1987).

Rienzi et al., "Predictive Value of Oocyte Morphology in Human IVF: A Systematic Review of the Literature," *Hum. Reprod. Update* 17(1):33-45 (2011).

Romiti et al., "Neutral/Alkaline and Acid Ceramidase Activities Are Actively Released by Murine Endothelial Cells," *Biochem. Biophys. Res. Comm.* 275:746-51 (2000).

Roudebush et al, "Embryonic Platelet-Activating Factor: An Indicator of Embryo Viability," *Hum. Reprod.* 17(5):1306-10 (2002).

Rousseau et al., "Utilization of Membranous Lipid Substrates by Membranous Enzymes: Activation of the Latent Sphingomyelinase of Hen Erythrocyte Membrane," *Arch. Biochern. Biophys.* 244(2):838-45 (1986).

Sands et al., "Biodistribution, Kinetics, and Efficacy of Highly Phosphorylated and Non-Phosphorylated Beta-Glucuronidase in the Murine Model of Mucopolysaccharidosis VII," *J. Biol. Chem.* 276(46):43160-5 (2001).

Schindler et al., "Neuroaxonal Dystrophy Due to Lysosomal Alpha-N-Acetylgalactosaminidase Deficiency," *New Eng. J. Med.* 320(26):1735-1740 (1989).

Schram et al., "The Identity of Alpha-Galactosidase B From Human Liver," *Biochimica et Biophysica Acta.* 482(1):138-144 (1977).

Schuchman et al., "Human Acid Sphingomyelinase. Isolation, Nucleotide Sequence and Expression of the Full-Length and Alternatively Spliced cDNAs," *J. Biol. Chem.* 266(13):8531-8539 (1991).

Schuchman et al., "A Novel Use for Acid Ceramidase in Cell-Based Therapies for Degenerative Joint Diseases, Including the Mucopolysaccharidoses," *Molecular Genetics and Metabolism* 105:S56 (2012) (abstract only).

Schuchman et al., "Pentosan Polysulfate: A Novel Therapy for the Mucopolysaccharidoses," *PLOS ONE* 8(1):e54459.

Scriver et al., Part 16: Lysosomal Disorders in: The Metabolic and Molecular Bases of Inherited Disease, 8th ed., McGraw-Hill (2000).

Second Office Action and English Translation for Chinese Patent Application No. 201280037341.5 (dated Nov. 3, 2015).

Seelan et al., "Human Acid Ceramidase is Overexpressed but Not Mutated in Prostate Cancer," *Genes Chromosomes & Cancer* 29:137 (2000).

Ségui et al., "Stress-Induced Apoptosis is Not Mediated by Endolysosomal Ceramide," *FASEB J.* 14:36-47 (2000).

Seli et al., "Noninvasive Metabolomic Profiling of Embryo Culture Media Using Proton Nuclear Magnetic Resonance Correlates With Reproductive Potential of Embryos in Women Undergoing in vitro fertilization," *Fertil. Steril.* 90:2183-89 (2008).

Sen et al., "Developments in Directed Evolution for Improving Enzyme Functions," *Appl. Biochem. Biotechnol.* 143:212-223 (2007).

Simonaro et al., "Involvement of the Toll-like Receptor 4 Pathway and Use of TNF-alpha Antagonists for Treatment of the Mucopolysaccharidoses," *PNAS* 107(1):222-227 (2010).

Springer et al., "Traffic Signals for Lymphocyte Recirculation and Leukocyte Emigration: The Multistep Paradigm," *Cell* 76(2):301-14 (1994).

Stahl et al., "Evidence for Receptor-Mediated Binding of Glycoproteins, Glycoconjugates, and Lysosomal Glycosidases by Alveolar Macrophages," *Proc. Natl. Acad. Sci. USA* 75(3):1399-403 (1978).

Strelow et al., "Overexpression of Acid Ceramidase Protects from Tumor Necrosis Factor-Induced Cell Death," *J. Exp. Med.* 192(5):601-11 (2000).

Supplementary European Search Report for European Patent Application No. 13797635.3 (dated Jan. 22, 2016).

Sweeley et al., "Post-Translational Processing Reactions Involved in the Biosynthesis of Lysosomal Alpha-N-Acetylgalactosaminidase in Cultured Human Fibroblasts," *Archives of Biochem & Biophys.* 233(1):158-65 (1983).

Tang et al., "Identification of PECAM-1 in Solid Tumor Cells and Its Potential Involvement in Tumor Cell Adhesion to Endothelium," *J. Biol. Chem.* 268(30):22883-22894 (1993).

Taylor et al., "Decreased Lysosomal Storage in the Adult MPS VII Mouse Brain in the Vicinity of Grafts of Retroviral Vector-Corrected Fibroblasts Secreting High Levels of Beta-Glucuronidase," *Nature Med.* 3(7): 771-74 (1997).

Thon et al., "The Murine TRAIL Receptor Signals Caspase-Independent Cell Death Through Ceramide," *Experimental Cell Research* 312:3808-21 (2006).

Tsuji et al., "Molecular Cloning of a Full-Length cDNA for Human Alpha-N-Acetylgalactosaminidase (alpha-galactosidase B)," *Biochem. Biophys. Res. Commun.* 163(3):1498-1504 (1989).

(56) References Cited

OTHER PUBLICATIONS

Tsuji et al. "Signal Sequence and DNA-Mediated Expression of Human Lysosomal Alpha-Galactosidase A," *Eur. J. Biochem.* 165(2):275-280 (1987).
UniProt_D7BW40 (last modified Aug. 10, 2010).
UniProt_Q19784 ( last modified Sep. 11, 2007).
UniProt_Q8YUN7 (last modified Mar. 1, 2002).
Vanier et al., "Niemann-Pick Diseases," Handbook of Clinical Neurology, 113(3rd series):1717-1721 (2013).
Vellodi et al., "Bone Marrow Transplantation for Mucopolysaccharidosis Type I: Experience of Two British Centres," *Arch. Dis. Child.* 76(2):92-99 (1997).
Voraberger et al., "Cloning of the Human Gene for Intercellular Adhesion Molecule 1 and Analysis of its 5'-Regulatory Region," *J. Immunol.* 147(8):2777-2786 (1991).
Waheed et al., "Human Lysosomal Acid Phosphatase is Transported as a Transmembrane Protein to Lysosomes in Transfected Baby Hamster Kidney Cells," *EMBO J.* 7(8):2351-8 (1988).
Walia et al., "Autologous Transplantation of Lentivector/Acid Ceramidase-Transduced Hematopoietic Cells in Nonhuman Primates," *Human Gene Therapy* 22:679-687 (2011).
Wang et al., "Human Alpha-N -Acetylgalactosaminidase-Molecular Cloning, Nucleotide Sequence, and Expression of a Full-Length cDNA. Homology with Human Alpha-Galactosidase A Suggests Evolution From a Common Ancestral Gene," *J. Biol. Chem.* 265(35):21859-21866 (1990).
Wang et al., "Molecular Genetics of PKU in Orientals," *Am J. Hum. Genet.* 45 (4 Suppl) A228 (1989).
Wang et al., "Schindler Disease Biochemical and Molecular Characterization of a New Neuroaxonal Dystrophy Due to Alpha-N Acetylgalactosaminidase Deficiency," *Am. J. Hum. Genet.* 43 (3 Suppl):A99 (1988).
Wang et al., "Schindler Disease: The Molecular Lesion in the Alpha-N-Acetylgalactosaminidase Gene That Causes an Infantile Neuroaxonal Dystrophy," *J. Clin. Invest.* 86(5):1752-1756 (1990).
Weinreb et al., "Effectiveness of Enzyme Replacement Therapy in 1028 Patients with Type 1 Gaucher Disease After 2 to 5 Years of Treatment: A Report from the Gaucher Registry," *Am. J. Med.* 113:112-19 (2002).
Weinstein et al., "Primary Structure of Beta-Galactoside Alpha 2,6-Sialyltransferase. Conversion of Membrane-Bound Enzyme to Soluble Forms by Cleavage of the NH2-Terminal Signal Anchor," *J. Biol. Chem.* 262(36):17735-43 (1987).
Whisstock et al., "Prediction of Protein Function from Protein Sequence," *Q. Rev. Biophysics* 36(3):307-340 (2003).
Wiewrodt et al., "Size-Dependent Intracellular Immunotargeting of Therapeutic Cargoes Into Endothelial Cells," *Blood* 99(3):912-22 (2002).
Wishart et al., "A Single Mutation Converts a Novel Phosphotyrosine Binding Domain Into a Dual-Specificity Phosphatase," *J. Biol. Chem.* 270(45):26782-26785 (1995).
Witkowski et al., "Conversion of b-ketoacyl Synthase to a Malonyl Decarboxylase by Replacement of the Active Cysteine With Glutamine," *Biochemistry* 38:11643-11650 (1999).
Witsenburg et al., "Cumulative Live Birth Rates in Cohorts of Patients Treated With in Vitro Fertilization or Intracytoplasmic Sperm Injection," *Fertil. Steril.* 84(1):99-107 (2005).
Xu et al., "Golgi Alkaline Ceramidase Regulates Cell Proliferation and Survival by Controlling Levels of Sphingosine and S1P," *The FASEB Journal* 20:1813-25 (2006).
Yamauchi et al., "Molecular Cloning of Two Species of cDNAs for Human Alpha-N-Acetylgalactosaminidase and Expression in Mammalian Cells," *Biochem. Biophys. Res. Commun.* 170(1):231-37 (1990).
Yeyati et al., "Fluorescence-Based Selection of Retrovirally Transduced Cells in the Absence of a Marker Gene: Direct Selection of Transduced Type B Niemann-Pick Disease Cells and Evidence for Bystander Correction," *Hum. Gene Ther.* 6(8):975-83 (1995).
Young et al., "Sphingolipids: Regulators of Crosstalk Between Apoptosis and Autophagy," *J. Lipid. Res.* 54:5-19 (2013).
Zhang et al., "Delivery of Beta-Galactosidase to Mouse Brain Via the Blood-Brain Barrier Transferrin Receptor," *J. Pharmacol. Exp. Ther.* 313(3):1075-81 (2005).
Zhu et al., "Dexamethasone-Mediated up-Regulation of the Mannose Receptor Improves the Delivery of Recombinant Glucocerebrosidase to Gaucher Macrophages." *J. Pharmacol. Exp. Ther.* 308(2):705-11 (2004).
Grassmé et al., "Rhinoviruses Infect Human Epithelial Cells via Ceramide-Enriched Membrane Platforms," J. of Biological Chemistry 280(28)(Issue of Jul. 15):26256-26262 (2005).
Gassert et al., "Induction of Membrane Ceramides: A Novel Strategy to Interfere with T Lymphocyte Cytoskeletal Reorganization in Viral Immunosuppression," PLoS Pathogens 5(10):1-11 (2009).
Gulbins et al., "Ceramide, Membrane Rafts and Infections," J. Mol. Med. 82:357-363 (2004).
Simons et al., "Cholesterol, Lipid Rafts, and Disease," J. of Clinical Investigation 110(5):597-603 (2002).
Becker et al., "Ceramide in Pseudomonas aeruginosa Infections and Cystic Fibrosis," *Cell Physiol. Biochem.* 26:57-66 (2010).
Esen et al., "Mechanisms of *Staphylococcus aureus* Induced Apoptosis of Human Endothelial Cells," Apoptosis 6(6):431-439 (2001).
Grassmé et al., "Acidic Sphingomyelinase Mediates Entry of N. gonorrhoeae into Nonphagocytic Cells," Cell 91:605-615 (1997).
Grassmé et al., "Host Defense Against Pseudomonas aeruginosa Requires Cermaide-Rich Membrane Rafts," Nature Medicine 9(3):322-330 (2003).
Dreschers et al., "Infections with Human Rhinovirus Induce the Formation of Distinct Functional Membrane Domains," Cell Physiol. Biochem. 20:241-254 (2007).
English Translation and Notice of Reasons for Rejection for Japanese Application No. 2014-517125 (dated May 9, 2016).
Office Action for European Application No. 12803458.4 (dated Feb. 8, 2016).
Office Action for U.S. Appl. No. 14/343,150 (dated Feb. 27, 2017).
Gilbert et al., "Exogenous Sphingomyelinase Increases Collagen and Sulphated Glycosaminoglycan Production by Primary Articular Chondrocytes: An In Vitro Study," Arthritis Research & Therapy 8(4):R89 (2006).
English Translation and Notice of Reasons for Rejection of Japanese Patent Application No. 2015-515238 (dated Mar. 6, 2017).
Seikagaku, "Metabolism of Sphingolipids Centered on Ceramide," Biochemistry 83(6):495-505 (2011) (English abstract only).
English Translation and Fourth Office Action for Chinese Patent Application No. 201280037341.5 (dated Mar. 20, 2017).
English Translation and Second Office Action for Chinese Patent Application No. 201380031825.3 (dated Apr. 6, 2017).
English Translation and Notice of Reasons for Rejection for Japanese Patent Application No. 2014-517125 (dated Dec. 12, 2016).
Office Action for European Patent Application No. 14775400.6 (dated Jun. 14, 2017).
Office Action for European Patent Application No. 14775400.6 (Jun. 14, 2017).
Office Action for European Patent Application No. 12830086.0 (Oct. 2, 2017).
English Translation and Third Office Action for Chinese Patent Application No. 2013800318253 (dated Oct. 10, 2017)
Office Action for U.S. Appl. No. 14/343,150 (dated Sep. 22, 2017).
Sabatini et al., "Effects of Ceramide on Apoptosis, Proteoglycan Degradation, and Matrix Metalloproteinase Expression in Rabbit Articular Cartilage," Biochem. Biophys. Res. Comm. 267:438-444 (2000).
Schulze et al., "Overexpression and Mass Spectrometry Analysis of Mature Human Acid Ceramidase," Biol. Chem. 388:1333-43 (2007).

\* cited by examiner

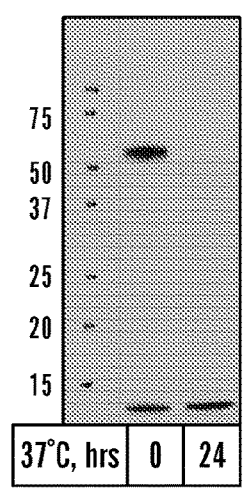 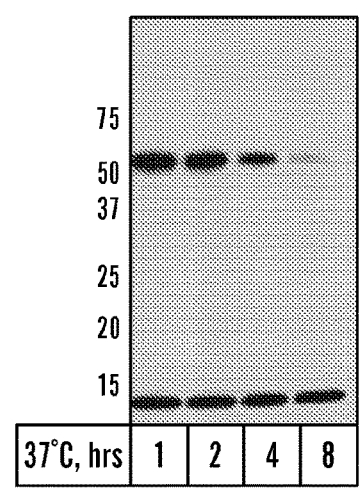
*FIG. 5A*  *FIG. 5B*

THERAPEUTIC ACID CERAMIDASE COMPOSITIONS AND METHODS OF MAKING AND USING THEM

This application is a national stage application under 35 U.S.C. § 371 of PCT Application No. PCT/US2014/026481, filed Mar. 13, 2014, which claims the benefit of U.S. Provisional Patent Application Serial No. 61/784,594, filed Mar. 14, 2013, which is hereby incorporated by reference in its entirety.

FIELD OF THE INVENTION

This invention relates to therapeutic acid ceramidase compositions and methods of making and using them.

BACKGROUND OF THE INVENTION

Due to its involvement in the human genetic disorder Farber Lipogranulomatosis ("FD"), Acid ceramidase ("AC;" N-acylsphingosine deacylase, I.U.B.M.B. Enzyme No. EC 3.5.1.23) is the most extensively studied member of the ceramidase enzyme family. The protein has been purified from several sources, and the human and mouse cDNAs and genes have been obtained (Bernardo et al., "Purification, Characterization, and Biosynthesis of Human Acid Ceramidase," *J. Biol. Chem.* 270:11098-102 (1995); Koch et al., "Molecular Cloning and Characterization of a Full-length Complementary DNA Encoding Human Acid Ceramidase. Identification of the First Molecular Lesion Causing Farber Disease," *J. Biol. Chem.* 2711:33110-5 (1996); Li et al., "Cloning and Characterization of the Full-length cDNA and Genomic Sequences Encoding Murine Acid Ceramidase," *Genomics* 50:267-74 (1998); Li et al., "The Human Acid Ceramidase Gene (ASAH): Chromosomal Location, Mutation Analysis, and Expression," *Genomics* 62:223-31 (1999)). Growing interest in the biology of this and other ceramidases stems from the fact that these enzymes play a central role in ceramide metabolism.

Ceramide is a signaling lipid that is produced in response to various stimuli and extrinsic factors, including serum deprivation and treatment with many chemotherapy drugs, as well as in many human diseases (Hannun, "Function of Ceramide in Coordinating Cellular Responses to Stress," *Science* 274:1855-9 (1996); Spiegel et al., "Signal Transduction Through Lipid Second Messengers," *Curr. Opin. Cell. Biol.* 8:159-67 (1996)). Inside cells, ceramide can influence growth and differentiation, regulate protein secretion, induce DNA fragmentation and apoptosis, and increase the synthesis and secretion of cytokines Normally present in low amounts, in response to these factors, ceramide is rapidly produced at the cell surface, leading to membrane re-organization and downstream signaling that results in apoptosis. After stimulation, AC and/or other ceramidases may then hydrolyze ceramide into the individual fatty acid and sphingosine components (Gatt, "Enzymic Hydrolysis and Synthesis of Ceramide," *J. Biol. Chem.* 238:3131-3 (1963); Gatt, "Enzymatic Hydrolysis of Sphingolipids. 1. Hydrolysis and Synthesis of Ceramides by an Enzyme from Rat Brain," *J. Biol. Chem.* 241:3724-31 (1966); Hassler & Bell, "Ceramidase: Enzymology and Metabolic Roles," *Adv. Lip. Res.* 26:49-57 (1993)). Because ceramide degradation is the only source of intracellular sphingosine (Rother et al., "Biosynthesis of Sphingolipids: Dihydroceramide and Not Sphinganine Is Desaturated by Cultured Cells," *Biochem. Biophys. Res. Commun.* 189:14-20 (1992)), these enzymes may also be rate-limiting steps in determining the intracellular levels of this compound. Importantly, a derivative of sphingosine, sphingosine-1-phosphate ("S1P"), can counteract the apoptotic effects of ceramide (Cuvillier et al., "Suppression of Ceramide-mediated Programmed Cell Death by Sphingosine-1-phosphate," *Nature* 381:800-3 (1996)), leading to the suggestion that ceramidases can be "rheostats" that maintain a proper balance between cell growth and death (Spiegel & Merrill, "Sphingolipids Metabolism and Cell Growth Regulation," *FASEB J.* 10:1388-97 (1996)).

AC hydrolyzes the amide bond linking the sphingosine and fatty acid moieties of the lipid ceramide (Park and Schuchman, "Acid Ceramidase and Human Disease," *Biochim. Biophys. Acta.* 1758(12): 2133-2138 (2006)). Ceramide, sphingosine (and its phosphorylated derivative S1P) are bioactive lipids, and thus the activity of AC must be carefully regulated in cells (Young et al., "Sphingolipids: Regulators of Crosstalk Between Apoptosis and Autophagy," *J. Lipid Res.* 54:5-19 (2013). One important mechanism by which AC activity is regulated is the cleavage of the inactive precursor polypeptide into the active enzyme consisting of an alpha and beta subunit linked via disulfide bonds (Shtraizent et al., "Autoproteolytic Cleavage and Activation of Human Acid Ceramidase," *J. Biol. Chem.* 283:11253-11259 (2008)). It has previously been shown that recombinant AC produced in Chinese Hamster ovary ("CHO") cells and secreted into the media is a mixture of inactive precursor and active (cleaved) enzyme (He et al., "Purification and Characterization of Recombinant, Human Acid Ceramidase," *J. Biol. Chem.* 278:32978-32986 (2003)).

The present invention is directed to overcoming these and other deficiencies in the art.

SUMMARY OF THE INVENTION

A first aspect of the present invention relates to a therapeutic composition including a ceramidase mixture and a pharmaceutically acceptable carrier. The ceramidase mixture includes an inactive acid ceramidase precursor and an active acid ceramidase.

A second aspect of the present invention relates to a method of acid ceramidase treatment, including formulating the acid ceramidase used in said treatment as a ceramidase mixture, where the ceramidase mixture includes an inactive acid ceramidase precursor and an active acid ceramidase.

A third aspect of the present invention relates to a method of producing a therapeutic composition. The method includes providing a medium containing an inactive acid ceramidase precursor and incubating the medium under conditions effective to transform a portion of the inactive acid ceramidase precursor to active acid ceramidase. The incubated medium is recovered as a ceramidase mixture comprising the inactive acid ceramidase precursor and an active acid ceramidase.

The present invention describes an optimal composition of recombinant AC (rAC). The present invention further describes the novel finding that, contrary to expectation, the fully active form of the enzyme is not the best form for promoting cell survival. Rather, preparations of purified rAC with higher amounts of inactive acid ceramidase (AC) precursor versus processed active AC are more effective at promoting cell survival and/or improving cell phenotype. Two preparations of recombinant AC were obtained containing different ratios of precursor and active enzyme. They were then used to evaluate the effects on the survival of oocytes in culture. Contrary to expectation, the preparation containing a higher ratio of inactive precursor had a greater effect on cell survival. It is hypothesized that this is due to the fact that the fully active enzyme has a shorter half-life in cells and in cell culture media. The same two preparations were tested using cultured primary chondrocytes. As with the oocytes, the preparation of recombinant AC with less of the active form had a greater effect on the expression of collagen 2, a marker of chondrogenesis.

rAC is being used experimentally in a number of cell systems and animal models to slow ceramide-related cell death and/or improve the phenotype of cells used for cell transplantation. It is also being studied in several disease models. The present invention describes the optimal preparation of rAC to be used for these purposes, which has numerous potential practical implications (e.g., in vitro fertilization, cartilage repair, and cystic fibrosis treatment).

In another derivative of the present invention, a novel method for the purification of recombinant AC was developed. In this method heat inactivation was used to remove acid sphingomyelinase and other contaminating proteins from the recombinant AC preparations. Previous work has shown that acid sphingomyelinase, a related lipid hydrolase, tightly binds to AC and co-purifies with it (Bernardo et al., "Purification, Characterization, and Biosynthesis of Human Acid Ceramidase," *J. Biol. Chem.* 270:11098-11102 (1995), which is hereby incorporated by reference in its entirety). It has now been found that unlike most proteins, AC activity is fully stable when heated at 60° C. Thus, after column chromatography heat inactivation can be used to remove acid sphingomyelinase activity from the recombinant AC preparation.

Together, these two novel findings regarding (i) the importance of maintaining an optimal ratio of precursor and active AC, and (ii) the use of heat inactivation to remove acid sphingomyelinase activity and other contaminating proteins from the preparation, constitute unique and important observations regarding the composition of recombinant AC.

BRIEF DESCRIPTION OF THE DRAWINGS

FIG. 1A is a western blot analysis showing the relative amounts of active (alpha/beta) versus inactive precursor rAC in two different bioreactor runs (Lot 6 and Lot 7). FIG. 1B summarizes results showing the ability of Lots 6 and 7 to form healthy mouse embryos. FIG. 1C depicts results of Lot 6 and Lot 7 after testing using cultured rat chondrocytes. At two weeks, the amount of collagen 2 expression was analyzed using western blotting.

FIGS. 5A-B are a Western blot showing conversion of inactive acid ceramidase to active acid ceramidase.

DETAILED DESCRIPTION OF THE INVENTION

Figure 1:
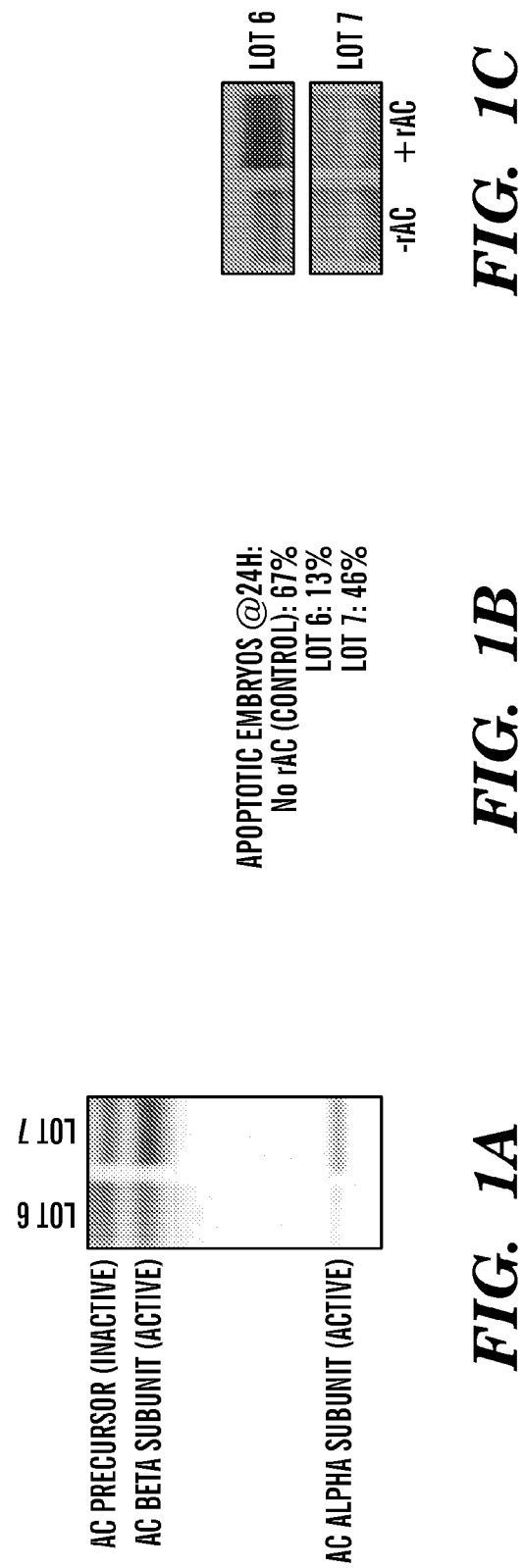
FIGS. 1A-1C show that preparations of rAC with less active ceramidase perform better than those with more active ceramidase.

A first aspect of the present invention relates to a therapeutic composition including a ceramidase mixture and a pharmaceutically acceptable carrier. The ceramidase mixture includes an inactive AC precursor and an active AC.

Ceramidases hydrolyze the amide linkage of ceramides to generate free fatty acids and sphingoid bases (Nikolova-Karakashian et al., "Ceramidases," *Methods Enzymol.* 311: 194-201 (2000); Hassler et al., "Ceramidases: Enzymology and Metabolic Roles," *Adv. Lipid Res.* 26:49-57 (1993), which are hereby incorporated by reference in their entirety). There are three types of ceramidases described to date (Nikolova-Karakashian et al., "Ceramidases," *Methods Enzymol.* 311:194-201 (2000), which is hereby incorporated by reference in its entirety). These are classified as acid, neutral, and alkaline ceramidases according to their pH optimum of enzymatic activity.

ACs have optimal enzymatic activity at a pH<5. The human AC was the first ceramidase to be cloned (Koch et al., "Molecular Cloning and Characterization of a Full-Length Complementary DNA Encoding Human Acid Ceramidase. Identification Of the First Molecular Lesion Causing Farber Disease," *J. Biol. Chem.* 271:33110-33115 (1996), which is hereby incorporated by reference in its entirety). It is localized in the lysosome and is mainly responsible for the catabolism of ceramide. Dysfunction of this enzyme because of a genetic defect leads to a sphingolipidosis disease called Lipogranulomatosis or Farber disease (Koch et al., "Molecular Cloning and Characterization of a Full-Length Complementary DNA Encoding Human Acid Ceramidase. Identification Of the First Molecular Lesion Causing Farber Disease," *J. Biol. Chem.* 271:33110-33115 (1996), Young et al., "Sphingolipids: Regulators of Crosstalk Between Apoptosis and Autophagy," *J. Lipid. Res.* 54:5-19 (2013), which is hereby incorporated by reference in its entirety).

Inactive AC precursors and active ACs suitable for use in the ceramidase mixtures of this and all aspects of the present invention can be homologous (i.e., derived from the same species) or heterologous (i.e., derived from a different species) to the tissue, cells, and/or subject being treated. Ceramidase (e.g., AC) precursor proteins undergo autoproteolytic cleavage into the active form (composed of α- and β-subunits). The mechanism of human AC cleavage and activation is reported in Shtraizent et al., "Autoproteolytic Cleavage and Activation of Human Acid Ceramidase," *J. Biol. Chem.* 283(17):11253-11259 (2008), which is hereby incorporated by reference in its entirety). This is promoted by the intracellular environment, and, based on highly conserved sequences at the cleavage site of ceramidase precursor proteins across species, is expected to occur in most, if not all, cell types. Thus, ceramidase as used herein includes both active ceramidases and ceramidase precursor proteins, where ceramidase precursor proteins are converted into active ceramidase proteins through autoproteolytic cleavage. Embodiments in which the precursor protein is taken up by the cell of interest and converted into active ceramidase thereby, as well as embodiments in which the precursor protein is converted into active ceramidase by a different cell or agent (present, for example, in a culture medium), are both contemplated.

AC (N-acylsphingosine deacylase, I.U.B.M.B. Enzyme No. EC 3.5.1.23) protein has been purified from several sources, and the human and mouse cDNAs and genes have been obtained. See Bernardo et al., "Purification, Characterization, and Biosynthesis of Human Acid Ceramidase," *J. Biol. Chem.* 270:11098-102 (1995); Koch et al., "Molecular Cloning and Characterization of a Full-length Complementary DNA Encoding Human Acid Ceramidase. Identification of the First Molecular Lesion Causing Farber Disease," *J. Biol. Chem.* 2711:33110-5 (1996); Li et al., "Cloning and Characterization of the Full-length cDNA and Genomic Sequences Encoding Murine Acid Ceramidase," *Genomics*

50:267-74 (1998); Li et al., "The Human Acid Ceramidase Gene (ASAH): Chromosomal Location, Mutation Analysis, and Expression," *Genomics* 62:223-31 (1999), all of which are hereby incorporated by reference in their entirety. It is produced through cleavage of the AC precursor protein (see Ferlinz et al., "Human Acid Ceramidase: Processing, Glycosylation, and Lysosomal Targeting," *J. Biol. Chem.* 276 (38):35352-60 (2001), which is hereby incorporated by reference in its entirety), which is the product of the Asah1 gene (NCBI UniGene GeneID No. 427, which is hereby incorporated by reference in its entirety). AC protein [*Homo sapien*] (Accession No. AAC50907) is shown below in SEQ ID NO: 1.

```
                                                              (SEQ ID NO: 1)
   1 mpgrscvalv llaaavscav aqhappwted crkstyppsg ptyrgavpwy tinldlppyk 61 rwhelmldka pmlkvivnsl knmintfvps gkvmqvvdek lpgllgnfpg pfeeemkgia 121 avtdiplgei isfnifyelf tictsivaed kkghlihgrn mdfgvflgwn inndtwvite 181 qlkpltvnld fqrnnktvfk assfagyvgm ltgfkpglfs ltlnerfsin ggylgilewi 241 lgkkdamwig fltrtvlens tsyeeaknll tktkilapay filggnqsge gcvitrdrke 301 sldvyeldak qgrwyvvqtn ydrwkhpffl ddrrtpakmc lnrtsqenis fetmydvlst 361 kpvlnkltvy ttlidvtkgq fetylrdcpd pcigw
```

The AC alpha subunit begins at the amino acid at position 22 and continues through position 142 (as shown in bold in SEQ ID NO: 1), while the beta subunit of the AC begins with the amino acid at position 143 and continues through position 395 (as shown in italics in SEQ ID NO: 1).

Active ACs and inactive AC precursor proteins that can be used in this and all aspects of the present invention include, without limitation, those set forth in Table 1 below.

TABLE 1

Exemplary Acid Ceramidase Family Members

| *Homo sapiens* (SEQ ID NO: 1) | | *Caenorhabditis elegans* (SEQ ID NO: 5) | |
|---|---|---|---|
| UniProt | Q13510, Q9H715, Q96AS2 | UniProt | O45686 |
| OMIM | 228000 | IntAct | O45686 |
| NCBI Gene | 427 | NCBI Gene | 173120 |
| NCBI RefSeq | NP_808592, NP_004306 | NCBI RefSeq | NP_493173 |
| NCBI RefSeq | NM_177924, NM_004315 | NCBI RefSeq | NM_060772 |
| NCBI UniGene | 427 | NCBI UniGene | 173120 |
| NCBI Accession | Q13510, AAC73009, AAC50907 | NCBI Accession | O45686, CAB05556 |
| *Mus musculus* (SEQ ID NO: 2) | | *Danio rerio* (SEQ ID NO: 6) | |
| UniProt | Q9WV54, Q3U8A7, | UniProt | Q5XJR7 |
| NCBI Gene | 11886 | NCBI Gene | 450068 |
| NCBI RefSeq | NP_062708 | NCBI RefSeq | NP_001006088 |
| NCBI RefSeq | NM_019734 | NCBI RefSeq | NM_001006088 |
| NCBI UniGene | 11886 | NCBI UniGene | 450068 |
| NCBI Accession | AK151208, AK034204 | NCBI Accession | AAH83231, CB360968 |
| *Gallus gallus* (SEQ ID NO: 3) | | *Rattus norvegicus* (SEQ ID NO: 7) | |
| UniProt | Q5ZK58 | UniProt | Q6P7S1, Q9EQJ6 |
| NCBI Gene | 422727 | NCBI Gene | 84431 |
| NCBI RefSeq | NP_001006453 | NCBI RefSeq | NP_445859 |
| NCBI RefSeq | NM_001006453 | NCBI RefSeq | NM_053407 |
| NCBI UniGene | 422727 | NCBI UniGene | 84431 |
| NCBI Accession | CAG31885, AJ720226 | NCBI Accession | AAH61540, AF214647 |
| *Pan troglodytes* (SEQ ID NO: 4) | | | |
| NCBI Gene | 464022 | | |
| NCBI RefSeq | XP_519629 | | |
| NCBI RefSeq | XM_519629 | | |
| NCBI UniGene | 464022 | | |

The ceramidase mixture of the therapeutic composition may, in some embodiments, contain a greater amount of the inactive AC precursor than active AC. Alternatively, the ceramidase mixture of the therapeutic composition may, in some instances, contain a lesser amount of inactive AC precursor than active AC.

In some embodiments, an effective amount of the inactive AC precursor compared to the active AC in the mixture ranges from about 5 to 95 wt % of the inactive AC precursor and 95 to 5 wt % of the active AC; 20 to 80 wt % of the inactive AC precursor and 80 to 20 wt % of the active AC; 30 to 70 wt % of the inactive AC precursor and 70 to 30 wt % of the active AC; 40 to 60 wt % of the inactive AC precursor and 60 to 40 wt % of the active AC; 55 to 95 wt % of the inactive AC precursor and 45 to 5 wt % of the active AC; 70 to 95 wt % of the inactive AC precursor and 30 to 5 wt % of the active AC; and may alternatively range from 80 to 90 wt % of the inactive AC precursor and 20 to 10 wt % of the active AC. An effective amount of the inactive AC precursor is 90 wt % while the active ceramidase is 10 wt % of the mixture. An alternative embodiment may include 80 wt % of the inactive ceramidase precursor and 20 wt % of the active AC in the ceramidase mixture. In yet a further embodiment, the ceramidase mixture may contain 60 wt % inactive ceramidase precursor and 40 wt % active ceramidase.

The therapeutic composition may also include pharmaceutically acceptable adjuvants, excipients, and/or stabilizers, and can be in solid or liquid form, such as tablets, capsules, powders, solutions, suspensions, or emulsions. Suitable adjuvants include, but are not limited to, flagellin, Freund's complete or incomplete adjuvant, aluminum hydroxide, lysolecithin, pluronic polyols, polyanions, peptides, oil emulsion, dinitrophenol, iscomatrix, and liposome polycation DNA particles.

A second aspect of the present invention relates to a method of AC treatment, including formulating the AC used in said treatment as a ceramidase mixture, where the ceramidase mixture includes an inactive AC precursor and an active AC.

Treatment according to this aspect of the present invention is carried out using methods that will be apparent to the skilled artisan. For a discussion of AC in the context of human disease, see Park et al., "Acid Ceramidase and Human Disease," *Biochim. Phiophys. Act.* 1758:2133-2138 (2006) and Zeidan et al., "Molecular Targeting of Acid Ceramidase: Implications to Cancer Therapy," *Curr. Drug Targets* 9(8):653-661 (2008), both of which are hereby incorporated by reference in their entirety).

In some embodiments, treatment is carried out by introducing a ceramidase protein into the cells. An approach for delivery of proteins or polypeptide agents (e.g., active ceramidase, inactive ceramidase precursor proteins) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins according to U.S. Pat. No. 5,817,789 to Heartlein et al., which is hereby incorporated by reference in its entirety. The chimeric protein can include a ligand domain and the polypeptide agent (e.g., rAC, active AC, other ceramidase, inactive AC precursor protein, other ceramidase precursor proteins). The ligand domain is specific for receptors located on a target cell. Thus, when the chimeric protein is delivered to the cell, the chimeric protein will adsorb to the targeted cell, and the targeted cell will internalize the chimeric protein.

Further embodiments of the present aspect relate to methods of treatment for a certain disease or disorder. These methods involve formulating the AC used in the treatment as a ceramidase mixture including an inactive ceramidase precursor and an active AC.

In one embodiment, the disease or disorder is a joint disease or disorder and the ceramidase mixture according to the methods of the present invention is administered to a subject to treat the subject for the joint disease or disorder. Exemplary types of joint disease or disorders include, without limitation, osteoarthritis, rheumatoid arthritis, mucopolysaccharidosis, degenerative joint disease, joint injury, and Farber lipogranulomatosis.

In another embodiment, the disease or disorder is a neurodegenerative disease or disorder and the ceramidase mixture according to the methods of the present invention is administered to a subject to treat the subject for the neurodegenerative disease or disorder. Exemplary types of neurodegenerative diseases or disorders include, without limitation, Alzheimer's disease, Frontotemporal Dementia, Dementia with Lewy Bodies, Prion disease, Parkinson's disease, Huntington's disease, Progressive Supranuclear Palsy, Corticobasal Degeneration, Multiple System Atrophy, amyotrophic lateral sclerosis, inclusion body myositis, degenerative myopathy, spinocerebellar atrophy, metabolic neuropathy, diabetic neuropathy, endocrine neuropathy, orthostatic hypotension, brain injury, spinal cord injury, stroke, and motor neuron diseases such as spinal muscular atrophy.

In another embodiment, the disease or disorder is a cardiac disease or disorder and the ceramidase mixture according to the methods of the present invention is administered to a subject to treat the subject for the cardiac disease or disorder. Exemplary types of cardiac diseases or disorders include, without limitation, heart disease, cardiac injury, atherosclerosis, thrombosis, cardiomyocyte apoptosis, hypercardia, heart infarction, mitral regurgitation, aortic regurgitation, septal defect, and tachycardia-bradycardia syndrome.

In another embodiment, the disease or disorder is diabetes and the ceramidase mixture according to the methods of the present invention is administered to a subject to treat the subject for diabetes.

In another embodiment, the disease or disorder is a pathogenic infection in a subject having cystic fibrosis, chronic obstructive pulmonary disease (COPD), and/or an open wound, and the ceramidase mixture according to the methods of the present invention is administered to a subject to treat the subject for the pathogenic infection. Exemplary types of pathogenic infections include, without limitation, viral, fungal, prionic, and bacterial.

Subjects suffering from cystic fibrosis, COPD, and/or an open wound, may possess a high susceptibility for acquiring acute and/or chronic pathogenic infections, such as, e.g., bacterial, viral, fungal, protozoan, and/or prionic pathogenic infections. Bacterial pathogens include, without limitation, *Bacillus anthracis, Bordetella pertussis, Borrelia burgdorferi, Campylobacter jejuni, Chlamydia trachomatis, Clostridium botulinum, Clostridium tetani, Corynebacterium dipththeriae, Escherichia coli,* enterohemorrhagic *E. coli,* enterotoxigenic *E. coli, Haemophilus influenzae* type B and non-typable, *Helicobacter pylori, Legionella pneumophila, Listeria monocytogenes, Mycobacterium* spp., *Mycobacterium leprae, Mycobacterium tuberculosis, Neisseria* gonorrhoeae, Neisseria meningitidis, Pneumococcus spp., Pseudomonas aeruginosa, Rickettsia, Salmonella spp., Shigella spp., Staphylococcus spp., Staphylococcus aureus, Streptococcus spp., Streptococcus pneumoniae, Streptococcus pyogenes, Streptococcus B, Group A beta hemolytic Streptococcus, Streptococcus mutans, Treponema pallidum, Vibrio cholerae, and Yersinia pestis. In some embodiments, the pathogenic infection is a Pseudomonas infection.

Viral pathogens include, without limitation, RNA viruses, DNA viruses, adenovirdiae (e.g., mastadenovirus and aviadeno virus), herpesviridae (e.g., herpes simplex virus 1, herpes simplex virus 2, herpes simplex virus 5, and herpes simplex virus 6), leviviridae (e.g., levivirus, enterobacteria phage MS2, allolevirus), poxyiridae (e.g., chordopoxyirinae, parapoxvirus, avipoxvirus, capripoxvirus, leporipoxvirus, suipoxvirus, molluscipox virus, and entomopoxyirinae), papovaviridae (e.g., polyomavirus and papillomavirus), paramyxoviridae (e.g., paramyxovirus, parainfluenza virus 1, mobillivirus such as measles virus, rubulavirus (such as mumps virus), pneumonoviridae (e.g., pneumovirus, human respiratory syncytial virus), metapneumovirus (e.g., avian pneumovirus and human metapneumo virus), picornaviridae (e.g., enterovirus, rhinovirus, hepatovirus such as human hepatitis A virus, cardiovirus, and apthovirus), reoviridae (e.g., orthoreo virus, orbivirus, rotavirus, cypo virus, fijivirus, phytoreo virus, and oryzavirus), retroviridae (e.g., mammalian type B retroviruses, mammalian type C retroviruses, avian type C retroviruses, type D retrovirus group, BLV-HTLV retroviruses, lentivirus (such as human immunodeficiency virus 1 and human immunodeficiency virus 2; and spuma virus), flaviviridae (e.g., hepatitis C virus), hepadnaviridae (e.g., hepatitis B virus), togaviridae (e.g., alphavirus—such as sindbis virus and rubivirus, such as rubella virus), rhabdoviridae (e.g., vesiculovirus, lyssavirus, ephemera virus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus), Cytomegalovirus (mononucleosis), Dengue virus (dengue fever, shock syndrome), Epstein-Barr virus (mononucleosis, Burkitt's lymphoma), Human T-cell lymphotropic virus type 1 (T-cell leukemia), Influenza A, B, and C (respiratory disease), Japanese encephalitis virus (pneumonia, encephalopathy), Poliovirus (paralysis), Rhinovirus (common cold), Rubella virus (fetal malformations), Vaccinia virus (generalized infection), Yellow fever virus (jaundice, renal and hepatic failure), and Varicella zoster virus (chickenpox).

Pathogenic fungi include, without limitation, the genera Aspergillus (e.g., Aspergillus fumigates), Blastomyces, Candida (e.g., Candida albicans), Coccidiodes, Cryptococcus, Histoplasma, Phycomyces, Tinea corporis, Tinea unguis, Sporothrix schenckii, and Pneumocystis carinii. Pathogenic protozoan include, without limitation, Trypanosome spp., Leishmania spp., Plasmodium spp., Entamoeba spp., and Giardia spp. such as Giardia lamblia.

As described herein, an "open wound" refers to a type of injury in which an epithelial layer, i.e., skin, is torn, cut, and/or punctured. In some embodiments, an open wound refers to a sharp injury which damages the dermis of the skin and concomitantly increases the chance of acquiring an infection. The term "open wound" also encompasses burns.

In another embodiment, the disease or disorder is an infection caused by ceramide accumulation and the ceramidase mixture according to the methods of the present invention is administered to a subject to treat the subject for the ceramide accumulation infection.

The present invention may, in other embodiments, be used to treat Farber disease.

In at least one embodiment, treatment is carried out in vitro. In this embodiment, a ceramidase mixture can be taken from the subject or from a second subject then administered to the first subject (e.g., by injecting the mixture into the first subject). In at least one embodiment, treatment is carried out in vivo.

Mammalian subjects according to these aspects of the present invention include, for example, human subjects, equine subjects, porcine subjects, feline subjects, and canine subjects. Human subjects are particularly preferred.

In all embodiments that involve administering the ceramidase mixture to a subject, any combination of active ceramidase, ceramidase precursor protein, and/or nucleic acid encoding ceramidase/ceramidase precursor protein can be administered. Administration can be accomplished either via systemic administration to the subject or via targeted administration to affected tissues, organs, and/or cells. The ceramidase mixture may be administered to a non-targeted area along with one or more agents that facilitate migration of the ceramidase mixture to (and/or uptake by) a targeted tissue, organ, or cell. Additionally and/or alternatively, the ceramidase mixture itself can be modified to facilitate its transport to (and uptake by) the desired tissue, organ, or cell, as will be apparent to one of ordinary skill in the art.

Typically, the ceramidase mixture will be administered to a subject in a vehicle that delivers the ceramidase to the target cell, tissue, or organ. Exemplary routes of administration include, without limitation, orally, by inhalation, intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, intrathecally, by application to mucous membranes (such as that of the nose, throat, bronchial tubes, genitals, and/or anus), or implantation of a sustained release vehicle.

In some embodiments, the ceramidase mixture is administered orally, topically, intranasally, intraperitoneally, intravenously, subcutaneously, or by aerosol inhalation. In some embodiments, the ceramidase mixture is administered via aerosol inhalation. In some embodiments, the ceramidase mixture can be incorporated into pharmaceutical compositions suitable for administration, as described herein.

The ceramidase mixture may be orally administered, for example, with an inert diluent, or with an assimilable edible carrier, or they may be enclosed in hard or soft shell capsules, or they may be compressed into tablets, or may be incorporated directly with the food of the diet. For oral therapeutic administration, the ceramidase mixture may be incorporated with excipients and used in the form of tablets, capsules, elixirs, suspensions, syrups, and the like. Such compositions and preparations should contain at least 0.1% of ceramidase. The percentage of ceramidase mixture in these compositions may, of course, be varied and may conveniently be between about 2% to about 60% of the weight of the unit. The amount of the ceramidase mixture in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as fatty oil.

The ceramidase mixture may also be administered parenterally. Solutions or suspensions of ceramidase can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The ceramidase mixture may also be administered directly to the airways in the form of an aerosol. For use as aerosols, ceramidase in solution or suspension may be packaged in a pressurized aerosol container together with suitable propellants, for example, hydrocarbon propellants like propane, butane, or isobutane with conventional adjuvants. The ceramidase mixture may also be administered in a non-pressurized form.

Exemplary delivery devices include, without limitation, nebulizers, atomizers, liposomes (including both active and passive drug delivery techniques) (Wang et al., "pH-Sensitive Immunoliposomes Mediate Target-cell-specific Delivery and Controlled Expression of a Foreign Gene in Mouse," *Proc. Nat'l Acad. Sci. USA* 84:7851-5 (1987); Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al.; Wolff et al., "The Use of Monoclonal Anti-Thy1 IgG1 for the Targeting of Liposomes to AKR-A Cells in Vitro and in Vivo," *Biochim. Biophys. Acta* 802: 259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of ceramidase to the desired organ, tissue, or cells.

Administration can be carried out as frequently as required and for a duration that is suitable to provide effective treatment. For example, administration can be carried out with a single sustained-release dosage formulation or with multiple daily doses.

Treatment according to this and all aspects of the present invention may be carried out in vitro or in vivo. In vivo treatments include, for example, embodiments in which the population of cells is present in a mammalian subject. In such embodiments the population of cells can be either autologous (produced by the subject), homologous, or heterologous. Suitable subjects according to these embodiments include mammals, e.g., human subjects, equine subjects, porcine subjects, feline subjects, and canine subjects.

In one embodiment, one or more additional agents which reduce ceramide levels may be administered with the ceramidase mixture. This includes, without limitation, inhibitors of acid sphingomyelinase (e.g., amitryptiline (Becker et al., "Acid Sphingomyelinase Inhibitors Normalize Pulmonary Ceramide and Inflammation in Cystic Fibrosis," *Am. J. Respir. Cell. Mol. Biol.* 42:716-724 (2010), which is hereby incorporated by reference in its entirety) and inhibitors of ceramide synthases (e.g., Shiffmann et al., "Inhibitors of Specific Ceramide Synthases," *Biochimie* 94:558-565 (2012), which is hereby incorporated by reference in its entirety)).

The effective amount of a therapeutic agent/cell population of the present invention administered to the subject will depend on the type and severity of the disease or disorder and on the characteristics of the individual, such as general health, age, sex, body weight, and tolerance to drugs. It will also depend on the degree, severity, and type of disease or disorder. The skilled artisan will be able to determine appropriate dosages depending on these and other factors.

In one embodiment of the present invention, the method includes treating one or more mammalian cells ex vivo with said ceramidase mixture to promote cell survival. Cells whose survival can be promoted according to this aspect of the present invention include, without limitation, those that utilize the ceramidase apoptosis pathway, which includes a wide variety of cells (Obeid et al., "Programmed Cell Death Induced by Ceramide," *Science* 259:1769-71 (1993), which is hereby incorporated by reference in its entirety), e.g., hepatocytes (Arora et al., "Ceramide Induces Hepatocyte Cell Death Through Disruption of Mitochondrial Function in the Rat," *Hepatol.* 25:958-63 (1997), which is hereby incorporated by reference in its entirety), skin fibroblasts (Mizushima et al., "Ceramide, a Mediator of Interleukin 1, Tumour Necrosis Factor α, as Well as Fas Receptor Signalling, Induces Apoptosis of Rheumatoid Arthritis Synovial Cells," *Ann. Rheum. Dis.* 57:495-9 (1998), which is hereby incorporated by reference in its entirety), chondrocytes (MacRae et al., "Ceramide Inhibition of Chondrocyte Proliferation and Bone Growth Is IGF-I Independent," *J. Endocrinol.* 191(2):369-77 (2006), which is hereby incorporated by reference in its entirety), lung epithelium (Chan & Goldkorn, "Ceramide Path in Human Lung Cell Death," *Am. J. Respir. Cell Mol. Biol.* 22(4):460-8 (2000), which is hereby incorporated by reference in its entirety), erythrocytes (Lang et al., "Mechanisms of Suicidal Erythrocyte Death," *Cell. Physiol. Biochem.* 15:195-202 (2005), which is hereby incorporated by reference in its entirety), cardiomyocytes (Parra et al., "Changes in Mitochondrial Dynamics During Ceramide-induced Cardiomyocyte Early Apoptosis," *Cardiovasc. Res.* (2007), which is hereby incorporated by reference in its entirety), and lymphocytes (Gombos et al., "Cholesterol and Sphingolipids as Lipid Organizers of the Immune Cells' Plasma Membrane: Their Impact on the Functions of MHC Molecules, Effector T-lymphocytes and T-cell Death," *Immunol. Lett.* 104(1-2):59-69 (2006), which is hereby incorporated by reference in its entirety), eggs, embryos, neurons, sperm, synovial fibroblasts, and embryonic stem cells. Preferred cell types are eggs (fertilized or unfertilized), embryos, primary cells (e.g., neurons), sperm, synovial fibroblasts, and embryonic stem cells. Moreover, the ceramide apoptosis pathway appears to be conserved across mammalian species (Lee & Amoscato, "TRAIL and Ceramide," *Vitam. Horm.* 67:229-55 (2004);

see also, Samadi, "Ceramide-induced Cell Death in Lens Epithelial Cells," *Mol. Vis.* 13:1618-26 (2007) (humans); Parra et al., "Changes in Mitochondrial Dynamics During Ceramide-induced Cardiomyocyte Early Apoptosis," *Cardiovasc. Res.* (2007) (rat); de Castro E Paula et al., "Ceramide Inhibits Development and Cytokinesis and Induces Apoptosis in Preimplantation Bovine Embryos," *Mol. Reprod. Devel.*, DOI No. 10.1002/mrd.20841 (2007) (cows), each which is hereby incorporated by reference in its entirety). Therefore, it is expected that, for each of the cell types recited above, suitable cells include those of humans, monkeys, mice, rats, guinea pigs, cows, horses, sheep, pigs, dogs, and cats. This method may also be used to prolong the survival of eggs and/or embryos during in vitro fertilization procedures, facilitating the identification and selection of healthy embryos for reimplantation, especially for older human women and for veterinary breeding procedures.

Cells according to this aspect of the present invention can be provided by methods that will be apparent to the skilled artisan. By way of example, the cells can be obtained from an animal or from an existing ex vivo source (e.g., a tissue sample, a cell culture, etc.) using standard techniques. Treating cells ex vivo includes treating cells present in a homogeneous culture, as well as cells present in a heterogeneous culture (e.g., a tissue sample).

Inactive AC precursors and active ACs that can be used to prepare the ceramidase mixture in this and all aspects of the present invention include, without limitation, those set forth in Table 1, supra. In this and all aspects of the present invention (including the in vivo methods discussed below), the AC can be homologous (i.e., derived from the same species) or heterologous (i.e., derived from a different species) to the one or more cells being treated.

One embodiment of the present aspect of AC treatment relates to a method of producing chondrocytes with the ceramidase mixture. This method involves selecting a population of cells having the potential to differentiate into chondrocytes and treating the selected cell population with the ceramidase mixture to transform one or more of the cells in the selected population into chondrocytes.

Cells having the potential to differentiate into chondrocytes include bone marrow cells, fibroblasts, mesenchymal stem cells, and/or fibroblasts (see Mizushima et al., "Ceramide, a Mediator of Interleukin 1, Tumour Necrosis Factor α, as Well as Fas Receptor Signaling, Induces Apoptosis of Rheumatoid Arthritis Synovial Cells," *Ann. Rheum. Dis.* 57:495-9 (1998), which is hereby incorporated by reference in its entirety).

Chondrocytes according to this aspect of the present invention include, without limitation, articular chondrocytes, nasal chondrocytes, tracheal chondrocytes, meniscal chondrocytes, and aural chondrocytes. These include, for example, mammalian chondrocytes, e.g., human chondrocytes, equine chondrocytes, porcine chondrocytes, feline chondrocytes, and canine chondrocytes. Preferably, the chondrocytes are primary chondrocytes.

Suitable cells according to this and all other aspects of the present invention include mammalian cells, e.g., human cells, equine cells, porcine cells, feline cells, and/or canine cells. Human cells are particularly preferred.

In this and all aspects of the present invention involving cell populations, embodiments in which the cells are all of one type, as well as embodiments in which the population is a mixture of two or more cell types, are both contemplated.

The ceramidase mixture and methods of treating the populations of cells with ceramidase mixture include all those set forth supra.

Another embodiment of the present aspect of AC treatment relates to a method of promoting chondrogenesis with the ceramidase mixture. In one embodiment, this method further includes selecting a population of stem cells in need of differentiation into chondrocytes, treating the population of stem cells with the ceramidase mixture to enrich mesenchymal stem cells within the stem cell population, and treating the population of enriched mesenchymal stem cells with the ceramidase mixture to promote differentiation of mesenchymal stem cells into chondrocytes.

Suitable cells populations according to this aspect of the present invention include mammalian cells populations, e.g., human cells populations, equine cells populations, porcine cells populations, feline cells populations, and/or canine cells populations. Human cells populations are particularly preferred.

Suitable stem cells according to this and all other aspects of the present invention include bone marrow cells, adipocytes, and skin cells. Additional stem cells according to this aspect of the present invention include, without limitation, embryonic stem cells, somatic stem cells, induced pluripotent stem cells, totipotent stem cells, pluripotent stem cells, and multipotent stem cells. Exemplary stem cells include, for example, hematopoietic stem cells, mesenchymal stem cells, neural stem cells, endothelial progenitor cells, epithelial stem cells, epidermal stem cells, adipocytes, and cardiac stem cells. Suitable stem cells include, but are not limited to, mammalian cells, e.g., human, equine, porcine, feline, and canine bone marrow cells, adipocytes, and skin cells. Human cells are particularly preferred.

Suitable chondrocytes are consistent with those described supra. The differentiated mesenchymal stem cells may, alternatively, be primary cells such as, but not limited to, neurons, hepatocytes, bone cells, lung cells, and cardiac cells.

In at least one embodiment, the number of differentiated cells in the cell population is maintained. In at least one embodiment, the number of differentiated cells in the cell population is increased. As will be apparent to the skilled artisan, maintaining or increasing the overall number of differentiated cells in the population can be achieved by decreasing or preventing de-differentiation of cells in the population that are already differentiated, by stimulating the differentiation of undifferentiated cells in the population, or both.

The ceramidase mixture and methods of treating the populations of cells with ceramidase mixture include all those set forth supra.

A third aspect of the present invention relates to a method of producing a therapeutic composition. The method includes providing a medium containing an inactive AC precursor; incubating the medium under conditions effective to transform a portion of the inactive AC precursor to active AC; and recovering the incubated medium as a ceramidase mixture comprising the inactive AC precursor and an active AC.

The therapeutic composition of the present invention contains a recombinant protein including both inactive AC precursor and active AC. The recombinant protein of the present invention may be prepared for use in the above described methods of the present invention using standard methods of synthesis known in the art, including solid phase peptide synthesis (Fmoc or Boc strategies) or solution phase peptide synthesis. Alternatively, proteins of the present invention may be prepared using recombinant expression systems.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation into a suitable host cell.

A variety of genetic signals and processing events that control many levels of gene expression (e.g., DNA transcription and messenger RNA ("mRNA") translation) can be incorporated into the nucleic acid construct to maximize peptide production. For the purposes of expressing a cloned nucleic acid sequence encoding a desired recombinant protein, it is advantageous to use strong promoters to obtain a high level of transcription. Depending upon the host system utilized, any one of a number of suitable promoters may be used. For instance, when cloning in $E.\ coli$, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other $E.\ coli$ promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. Mammalian cells that may be used for manufacture of the recombinant protein of the present invention include, for example, Chinese Hamster Ovary (CHO) cells, plant cells, chicken eggs, and human fibroblasts.

There are other specific initiation signals required for efficient gene transcription and translation in prokaryotic cells that can be included in the nucleic acid construct to maximize peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding a recombinant protein of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety.

Once the nucleic acid molecule encoding the peptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified peptides may be obtained by several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. In one embodiment of the present invention, cells may be transformed with DNA encoding AC and then cultured under conditions effective to produce the medium containing inactive AC precursor. The fraction containing the peptide is subjected to gel filtration in an appropriately sized dextran or polyacrylamide column to separate the peptides from other proteins. If necessary, the peptide fraction may be further purified by other chromatography.

In one embodiment of the present invention, the incubation is carried out under conditions effective to reduce the transformation rate of inactive AC precursor to active AC compared to the transformation rate achieved when said incubating is carried out at a pH of 4 and a temperature of 4° C. or 37° C., for 24 hours, under otherwise consistent conditions. Alternatively, the incubating may be carried out under conditions effective to enhance the transformation rate of inactive AC precursor to active AC compared to those same conditions.

In some embodiments, the ceramidase mixture during the incubating may have a pH over 4.0 and up to 6.5. The mixture may, for example, have a pH of 4.0, 4.5, 5.0, 5.5, 6.0, or 6.5. In other embodiments, the temperature of the ceramidase mixture during said incubating may be at least −30° C. and under 37° C. The temperature of the mixture may, for example, be −30° C., −25° C., −20° C., −15° C., −10° C., −5° C., 0° C., 5° C., 10° C., 15° C., 20° C., 25° C., 30° C., or 35° C. Alternatively, the mixture may be incubated under conditions of −30° C. with a pH of 4.0, 4° C. with a pH of 4.0 or 6.5, 25° C. with a pH of 4.0, or 37° C. with a pH of 4.0. The mixture may be incubated for a period of time such as, but not limited to, approximately 30 minutes, 1 hour, 3 hours, 30 hours, or 300 hours.

During incubation of this aspect of the present invention, the medium may be heated under conditions effective to remove acid sphingomyelinase activity. In this embodiment, the medium may be heated to 60° C. for a period of time including, but not limited to, less than 20 minutes, 20-40 minutes, 40-60 minutes, or more than 60 minutes.

It is to be appreciated that certain aspects, modes, embodiments, variations and features of the present invention are described in various levels of detail in order to provide a substantial understanding of the present technology. The definitions of certain terms as used in this specification are also provided. Unless defined otherwise, all technical and scientific terms used herein generally have the same meaning as commonly understood by one of ordinary skill in the art to which this invention belongs.

EXAMPLES

The following examples are provided to illustrate embodiments of the present invention but are by no means intended to limit its scope.

Example 1

Materials and Methods

Preparation of rAC (Lot 6 and Lot 7)—Chinese hamster ovary cells overexpressing the human Asah1 gene were generated and rAC was purified from the media (He et al., "Purification and Characterization of Recombinant, Human Acid Ceramidase. Catalytic Reactions and Interactions With Acid Sphingomyelinase," *J. Biol. Chem.* 278:32978-32986 (2003), which is hereby incorporated by reference in its entirety). No in vitro manipulation was carried out after purification of Lot 6 (higher amount of inactive AC precursor). After purification of Lot 7 enzyme, the rAC was incubated in pH 4 citrate phosphate buffer at 37° C. for three hours.

Comparison of Lot 6 and Lot 7 for Mouse Embryo Production—Methods for using rAC for mouse embryo production are described in Eliyahu et al., "Acid Ceramidase Improves the Quality of Oocytes and Embryos and the Outcome of In Vitro Fertilization," *FASEB J.* 24:1229-1238 (2010), which is hereby incorporated by reference in its entirety. Sperm and mature oocytes were obtained from C57 Black mice and in vitro fertilization was carried out using equal amounts of Lot 6 and Lot 7 enzyme.

Comparison of Lot 6 and Lot 7 to Improve the Chondrogenic Phenotype of Rat Articular Chondrocytes—Equal amounts of Lot 6 and Lot 7 rAC were added to the media of primary articular chondrocytes isolated from femurs. Cartilage was digested and cells were placed into culture with and without rAC supplementation. After three days the media was changed to media without rAC. Cells were grown for an additional two weeks and the levels of collagen 2 (marker of mature articular chondrocytes) was determined by western blotting.

Example 2 rAC with Less Active AC Perform Better than Those with More Active AC

Preparations of rAC with less active ceramidase perform better than those with more active ceramidase (FIGS. 1A-1C). As indicated in FIG. 1A, a western blot analysis showed the relative amounts of active (alpha/beta) versus inactive precursor rAC in two different bioreactor runs (Lot 6 and Lot 7). Lot 7 had more active rAC than in Lot 6. In vitro examples (IVF and chondrocytes) compared two rAC preparations with ratios that were approximately 90:10 (inactive:active) (Lot 6) versus approximately 80:20 (inactive:active) (Lot 7) (FIG. 1A). Apoptosis was determined at 24 hours using standard morphological methods (e.g., membrane integrity, etc.) (Eliyahu et al., "Acid Ceramidase Improves the Quality of Oocytes and Embryos and the Outcome of In Vitro Fertilization," *FASEB J.* 24:1229-1238 (2010), which is hereby incorporated by reference in its entirety).

FIG. 1B summarizes results for ability to form healthy mouse embryos in Lot 6 and Lot 7. Lot 7 (containing more active rAC) produced more apoptotic embryos than lot 6 (containing less active rAC). As can be seen in FIG. 1B, the preparation with less active enzyme (Lot 6) provided better results in IVF (fewer apoptotic embryos). This was unexpected.

Lot 6 and Lot 7 were also tested using cultured rat chondrocytes (FIG. 1C). At two weeks the amount of collagen 2 expression was analyzed using western blotting. Cells cultured with Lot 7 (more active rAC) produced less collagen 2. Lot 6 was better in maintaining the chondrocyte phenotype after expansion (FIG. 1C, based on the expression of collagen 2). This was unexpected.

The improved performance of rAC containing less active AC is hypothesized to be due to the shorter half-life of the active enzyme in cultured cells (conversely the longer half-life of the precursor).

In order to manipulate the ratio of inactive to active enzyme, pH was adjusted to 4.0 and the preparation was incubated at 37° C. Under these conditions an increase of approximately 10% active enzyme was observed for every 3 hours of incubation. Thus, to covert a preparation that is 90:10 inactive:active to 100% active, the preparation is incubated for 27 hours.

An important variable here is temperature. If the preparations are maintained (pH adjusted) frozen, there is no conversion. If the preparations are maintained at 4° C. (in a refrigerator) the conversion proceeds but at 1% the efficiency of 37° C. (10% increase in active enzyme requires 300 versus 3 hours). If the preparation is maintained at room temperature (25° C.), it proceeds at 10% the efficiency (10% increase requires 30 hours). If the pH is not acidified, there is no conversion at 4° C. and only 1% conversion rate (300 hours are required for an increase of 10%) at room temperature.

Example 3

Removal of Contaminating Acid Sphingomyelinase Activity from rAC

Figure 2:
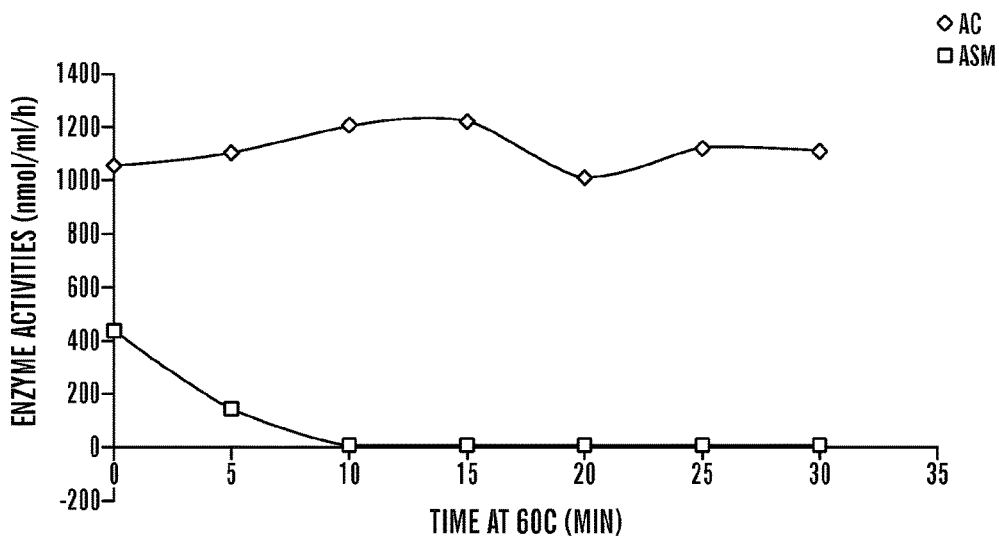
FIG. 2 illustrates a time-response curve of AC and acid sphingomyelinase activity in Lot 7. Acid sphingomyelinase activity was removed without affecting AC activity.

Methods of removing contaminating acid sphingomyelinase activity (ASM) from the rAC preparations were developed. This requires incubation of the final rAC preparations at 60° C. for 10-20 minutes. This incubation does not affect rAC (activity or ratio of inactive to active) but removes all ASM activity, which is essential to manufacturing (FIG. 2).

Example 4

Figure 3:
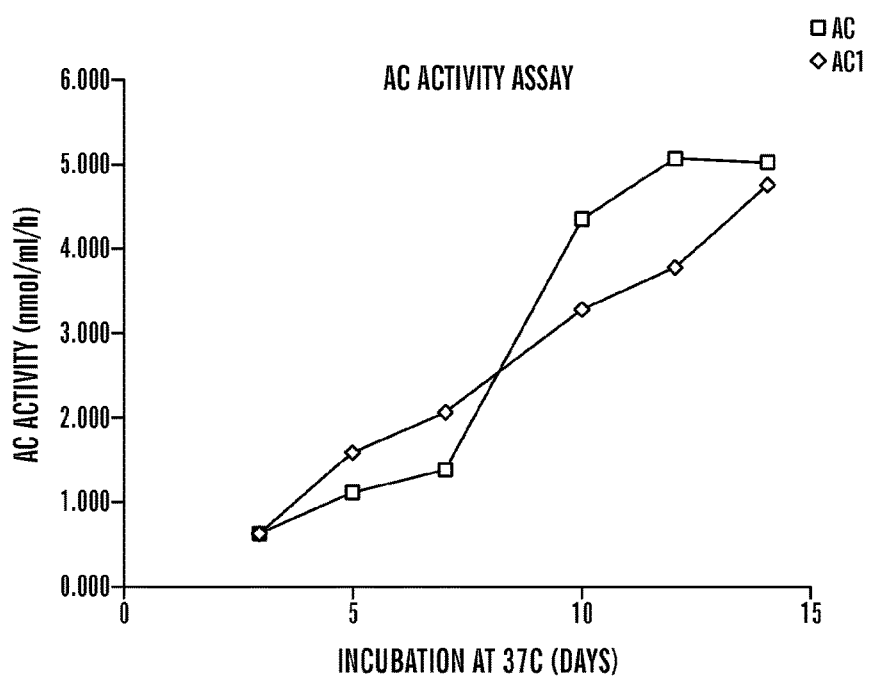
FIG. 3 is a plot of acid ceramidase activity in (nmol/ml/hour) versus incubation time (in days).
Figure 4:
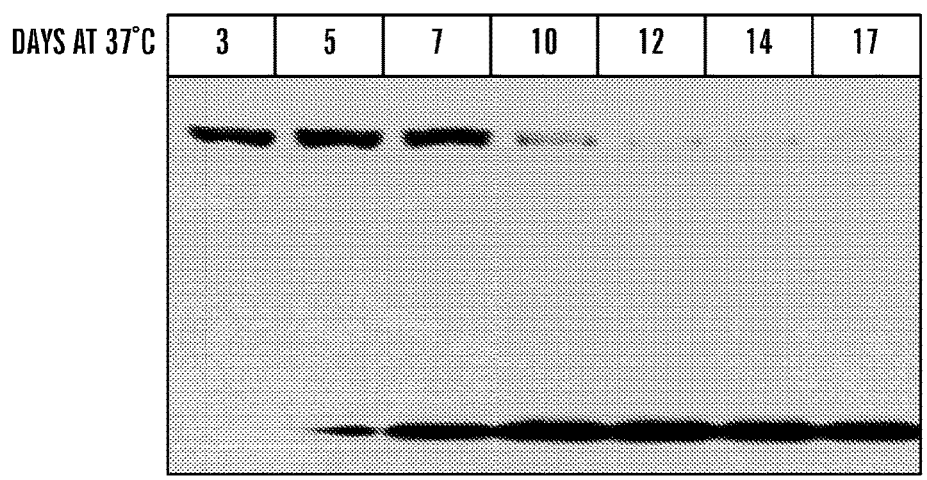
FIG. 4 is a Western blot showing conversion of inactive acid ceramidase to active acid ceramidase.

Incubation of Media Containing Recombinant Human Acid Ceramidase at 37° C. for Varying Lengths of Time Conditioned media (DMEM, pH 6.8 containing 10% fetal calf serum) was collected from Chinese hamster ovary cells overexpressing and secreting recombinant human acid ceramidase (rhAC) (He et al., "Purification and Characterization of Recombinant, Human Acid Ceramidase. Catalytic Reactions and Interactions With Acid Sphingomyelinase," *J. Biol. Chem.* 278:32978-32986 (2003), which is hereby incorporated by reference in its entirety). The cells were grown until ~100% confluency in T-75 mm flasks, and media was then collected after 4 days of additional growth. The collected media was filtered through 0.22 mm membranes to removed debris and placed in a 37° C. incubator for varying lengths of time. At the end of the incubation period the media was frozen at −20° C. prior to assay. AC activity (FIG. 3) was determined as previously described (He et al., *Anal Biochem,* 274:264 (1999), which is hereby incorporated by reference in its entirety): reaction mixtures were incubated at 37° C. for one hour. AC Western Blot (FIG. 4): 6.5 μl/lane, was developed using a mouse anti-human AC monoclonal antibody (1:300, #SC136275, Santa Cruz) against the alpha-subunit. This data shows that in vitro incubation of media containing rhAC at 37° C. for 3-17 days, resulting in conversion of inactive precursor into active enzyme (represented by the alpha subunit and an increase in enzymatic activity).

Example 5

In Vitro Conversion of Purified, Recombinant Human Acid Ceramidase at 37° C.

Purified recombinant human AC (rhAC; 4 ug/ul in EMEM, pH 6.8) was isolated from the media of overexpressing Chinese hamster ovary cells as previously described (He et al., "Purification and Characterization of Recombinant, Human Acid Ceramidase. Catalytic Reactions and Interactions With Acid Sphingomyelinase," *J. Biol. Chem.* 278:32978-32986 (2003), which is hereby incorporated by reference in its entirety). AC Western Blot (FIG. 5): 6.5 μl/lane, was developed using a mouse anti-human AC monoclonal antibody against the alpha-subunit (1:300, #SC136275, Santa Cruz). This data shows that in vitro incubation of purified rhAC at 37° C. for 24 h (FIG. 5A) resulted in complete conversion of the precursor to active form. Incubation from 1-8 hours (FIG. 5B) showed a linear progression of conversion.

Although the invention has been described in detail for the purpose of illustration, it is understood that such detail is solely for that purpose, and variations can be made therein by those skilled in the art without departing from the spirit and scope of the invention which is defined by the following claims.

---

What is claimed:

1. A therapeutic composition comprising a ceramidase mixture comprising:
   a recombinant inactive acid ceramidase precursor and
   a recombinant active acid ceramidase; and
   a pharmaceutically acceptable carrier;
   wherein the amount of said inactive acid ceramidase precursor is greater than the amount of said active ceramidase in said ceramidase mixture, and wherein said therapeutic composition has no detectable acid sphingomyelinase activity.

2. The therapeutic composition of claim 1, wherein said ceramidase mixture comprises 55 to 95 wt % of said inactive acid ceramidase precursor and 45 to 5 wt % of said active acid ceramidase.

3. The therapeutic composition of claim 1, wherein said ceramidase mixture comprises 70 to 95 wt % of said inactive acid ceramidase precursor and 30 to 5 wt % of said active acid ceramidase.

4. The therapeutic composition of claim 1, wherein said ceramidase mixture comprises 80 to 90 wt % of said inactive ceramidase precursor and 20 to 10 wt % of said active acid ceramidase.

5. The therapeutic composition of claim 1, further comprising an adjuvant.

6. The therapeutic composition of claim 5, wherein said adjuvant is selected from the group consisting of flagellin, Freund's complete or incomplete adjuvant, aluminum hydroxide, lysolecithin, pluronic polyols, polyanions, peptides, oil emulsion, dintrophenol, iscomatrix, and lipsosome polycation DNA particles.

7. The therapeutic composition of claim 1, wherein said ceramidase mixture further comprises a nucleic acid encoding said active acid ceramidase protein, a nucleic acid encoding said inactive ceramidase precursor protein, or a combination thereof.

8. The therapeutic composition of claim 1, wherein said ceramidase mixture is in a form selected from tablets, capsules, elixirs, suspensions, a solution, a dispersion, or syrups.

9. The therapeutic composition of claim 1, wherein said ceramidase mixture further comprises one or more of the following: a binder, an excipient, a disintegrating agent, a lubricant, a sweetening agent, or a liquid carrier.

10. The therapeutic composition of claim 1, wherein said ceramidase mixture further comprises one or more of the following: a surfactant, glycerol, liquid polyethylene glycol, oil, saline, water, ethanol, a polyol, or a sugar solution.

11. The therapeutic composition of claim 1, wherein said ceramidase mixture is in an aerosol form.

12. The therapeutic composition of claim 11, wherein said aerosol form further comprises a propellant and an adjuvant.

13. The therapeutic composition of claim 1, further comprising an additional agent selected from inhibitors of acid sphingomyelinase, inhibitors of ceramide synthases, or a combination thereof.

14. The therapeutic composition of claim 1, wherein said active acid ceramidase and said inactive ceramidase precursor comprises the amino acid sequence selected from the group consisting of SEQ ID NO:1, SEQ ID NO: 2, SEQ ID NO: 3, SEQ ID NO: 4, SEQ ID NO: 5, SEQ ID NO:6, and SEQ ID NO:7.

15. The therapeutic composition of claim 1, wherein said ceramidase mixture is present in a therapeutically effective amount.

* * * * *

SEQUENCE LISTING

```
<160> NUMBER OF SEQ ID NOS: 7

<210> SEQ ID NO 1
<211> LENGTH: 395
<212> TYPE: PRT
<213> ORGANISM: Homo sapiens
<220> FEATURE:
<223> OTHER INFORMATION: acid ceramidase

<400> SEQUENCE: 1

Met Pro Gly Arg Ser Cys Val Ala Leu Val Leu Leu Ala Ala Ala Val
1               5                   10                  15

Ser Cys Ala Val Ala Gln His Ala Pro Pro Trp Thr Glu Asp Cys Arg
            20                  25                  30

Lys Ser Thr Tyr Pro Pro Ser Gly Pro Thr Tyr Arg Gly Ala Val Pro
        35                  40                  45

Trp Tyr Thr Ile Asn Leu Asp Leu Pro Pro Tyr Lys Arg Trp His Glu
    50                  55                  60

Leu Met Leu Asp Lys Ala Pro Met Leu Lys Val Ile Val Asn Ser Leu
65                  70                  75                  80

Lys Asn Met Ile Asn Thr Phe Val Pro Ser Gly Lys Val Met Gln Val
                85                  90                  95

Val Asp Glu Lys Leu Pro Gly Leu Leu Gly Asn Phe Pro Gly Pro Phe
            100                 105                 110

Glu Glu Glu Met Lys Gly Ile Ala Ala Val Thr Asp Ile Pro Leu Gly
        115                 120                 125

Glu Ile Ile Ser Phe Asn Ile Phe Tyr Glu Leu Phe Thr Ile Cys Thr
    130                 135                 140

Ser Ile Val Ala Glu Asp Lys Lys Gly His Leu Ile His Gly Arg Asn
```

```
                145                 150                 155                 160
Met Asp Phe Gly Val Phe Leu Gly Trp Asn Ile Asn Asn Asp Thr Trp
                    165                 170                 175

Val Ile Thr Glu Gln Leu Lys Pro Leu Thr Val Asn Leu Asp Phe Gln
                    180                 185                 190

Arg Asn Asn Lys Thr Val Phe Lys Ala Ser Ser Phe Ala Gly Tyr Val
                    195                 200                 205

Gly Met Leu Thr Gly Phe Lys Pro Gly Leu Phe Ser Leu Thr Leu Asn
        210                 215                 220

Glu Arg Phe Ser Ile Asn Gly Gly Tyr Leu Gly Ile Leu Glu Trp Ile
225                 230                 235                 240

Leu Gly Lys Lys Asp Ala Met Trp Ile Gly Phe Leu Thr Arg Thr Val
                245                 250                 255

Leu Glu Asn Ser Thr Ser Tyr Glu Glu Ala Lys Asn Leu Leu Thr Lys
                260                 265                 270

Thr Lys Ile Leu Ala Pro Ala Tyr Phe Ile Leu Gly Gly Asn Gln Ser
        275                 280                 285

Gly Glu Gly Cys Val Ile Thr Arg Asp Arg Lys Glu Ser Leu Asp Val
290                 295                 300

Tyr Glu Leu Asp Ala Lys Gln Gly Arg Trp Tyr Val Val Gln Thr Asn
305                 310                 315                 320

Tyr Asp Arg Trp Lys His Pro Phe Phe Leu Asp Arg Arg Thr Pro
                325                 330                 335

Ala Lys Met Cys Leu Asn Arg Thr Ser Gln Glu Asn Ile Ser Phe Glu
                340                 345                 350

Thr Met Tyr Asp Val Leu Ser Thr Lys Pro Val Leu Asn Lys Leu Thr
                355                 360                 365

Val Tyr Thr Thr Leu Ile Asp Val Thr Lys Gly Gln Phe Glu Thr Tyr
                370                 375                 380

Leu Arg Asp Cys Pro Asp Pro Cys Ile Gly Trp
385                 390                 395

<210> SEQ ID NO 2
<211> LENGTH: 394
<212> TYPE: PRT
<213> ORGANISM: Mus musculus
<220> FEATURE:
<223> OTHER INFORMATION: acid ceramidase

<400> SEQUENCE: 2

Met Arg Gly Gln Ser Leu Leu Thr Trp Val Leu Ala Ala Ala Val Thr
1               5                   10                  15

Cys Ala Gln Ala Gln Asp Val Pro Pro Trp Thr Glu Asp Cys Arg Lys
                20                  25                  30

Ser Thr Tyr Pro Pro Ser Gly Pro Thr Tyr Arg Gly Pro Val Pro Trp
            35                  40                  45

His Thr Ile Asn Leu Asp Leu Pro Pro Tyr Lys Arg Trp His Glu Leu
        50                  55                  60

Leu Ala Gln Lys Ala Pro Ala Leu Arg Ile Leu Val Asn Ser Ile Thr
65                  70                  75                  80

Ser Leu Val Asn Thr Phe Val Pro Ser Gly Lys Leu Met Lys Met Val
                85                  90                  95

Asp Gln Lys Leu Pro Gly Met Ile Gly Ser Leu Pro Asp Pro Phe Gly
                100                 105                 110

Glu Glu Met Arg Gly Ile Ala Asp Val Thr Gly Ile Pro Leu Gly Glu
```

```
            115                 120                 125
Ile Ile Ser Phe Asn Ile Phe Tyr Glu Leu Phe Thr Met Cys Thr Ser
130                 135                 140

Ile Ile Thr Glu Asp Glu Lys Gly His Leu Leu His Gly Arg Asn Met
145                 150                 155                 160

Asp Phe Gly Ile Phe Leu Gly Trp Asn Ile Asn Asn Asn Thr Trp Val
                165                 170                 175

Val Thr Glu Glu Leu Lys Pro Leu Thr Val Asn Leu Asp Phe Gln Arg
            180                 185                 190

Asn Asn Lys Thr Val Phe Lys Ala Thr Ser Phe Val Gly Tyr Val Gly
        195                 200                 205

Met Leu Thr Gly Phe Lys Pro Gly Leu Phe Ser Leu Ser Leu Asn Glu
    210                 215                 220

Arg Phe Ser Ile Asn Gly Gly Tyr Leu Gly Ile Leu Glu Trp Met Phe
225                 230                 235                 240

Gly Arg Lys Asp Ala Gln Trp Val Gly Phe Ile Thr Arg Ser Val Leu
                245                 250                 255

Glu Asn Thr Thr Ser Tyr Glu Glu Ala Lys Asn Thr Leu Thr Lys Thr
            260                 265                 270

Lys Ile Met Ala Pro Val Tyr Phe Ile Leu Gly Gly Lys Lys Ser Gly
        275                 280                 285

Glu Gly Cys Val Ile Thr Arg Glu Arg Lys Glu Ser Leu Asp Val Tyr
    290                 295                 300

Glu Leu Asp Pro Lys His Gly Arg Trp Tyr Val Val Gln Thr Asn Tyr
305                 310                 315                 320

Asp Arg Trp Lys Asn Thr Leu Phe Ile Asp Asp Arg Arg Thr Pro Ala
                325                 330                 335

Lys Lys Cys Leu Asn His Thr Thr Gln Lys Asn Leu Ser Phe Ala Thr
            340                 345                 350

Ile Tyr Asp Val Leu Ser Thr Lys Pro Val Leu Asn Lys Leu Thr Val
        355                 360                 365

Phe Thr Thr Leu Met Asp Val Thr Lys Gly Gln Phe Glu Ser His Leu
    370                 375                 380

Arg Asp Cys Pro Asp Pro Cys Ile Gly Trp
385                 390

<210> SEQ ID NO 3
<211> LENGTH: 395
<212> TYPE: PRT
<213> ORGANISM: Gallus gallus
<220> FEATURE:
<223> OTHER INFORMATION: acid ceramidase

<400> SEQUENCE: 3

Met Ala Gly Arg Gly Arg Ala Leu Leu Pro Pro Ala Val Leu Met Val
1               5                   10                  15

Leu Val Leu Val Val Ala Pro Asp Pro Tyr Gly Glu Asp Cys Arg
            20                  25                  30

Ser Lys Met Tyr Pro Pro Ser Gly Pro Thr Phe Lys Gly Asn Val Pro
        35                  40                  45

Thr Tyr Ile Ile Asn Leu Asp Leu Pro Pro Ser Lys Arg Trp Asp Glu
    50                  55                  60

Leu Ile Arg Ala Lys Lys Thr Glu Leu Lys Ala Val Ile Gln Asn Ile
65                  70                  75                  80

Lys Asp Ile Ala Asn Thr Phe Phe Pro Ser Gly Lys Ile Val Asp Ile
```

```
              85                  90                  95
Val Asp His Lys Ile Ser His Leu Thr Asp Thr Leu Pro Tyr Pro Phe
                100                 105                 110

Asn Glu Glu Leu Gln Gly Ile Ala Asn Ser Ser Gly Ile Pro Leu Gly
                115                 120                 125

Glu Ile Val Ile Phe Asn Ile Phe Tyr Glu Ile Phe Thr Val Cys Thr
            130                 135                 140

Ser Ile Val Ala Glu Asp Ser Arg Gly Lys Leu Tyr His Ala Arg Asn
145                 150                 155                 160

Leu Asp Phe Gly Leu Phe Leu Gly Trp Asp Val Lys Asn Asn Phe Trp
                165                 170                 175

Thr Val Thr Arg Glu Leu Lys Pro Thr Val Val Asn Leu Asp Phe Gln
                180                 185                 190

Arg Asn Asn Lys Thr Val Phe Arg Ser Thr Asn Phe Ala Gly Tyr Ile
                195                 200                 205

Gly Met Val Ser Gly Val Lys Pro Asp Leu Phe Thr Leu Thr Met Asn
            210                 215                 220

Glu Arg Phe Ser Leu Asp Gly Gly Tyr Ile Gly Ile Phe Glu Trp Phe
225                 230                 235                 240

Leu Gly Arg Arg Asp Gly Met Trp Met Gly Phe Leu Thr Arg Ser Val
                245                 250                 255

Leu Glu Asn Ala Thr Ser Tyr Gln Asp Ala Lys Asp Lys Leu Ala Lys
                260                 265                 270

Thr Arg Leu Leu Ala Pro Ala Tyr Phe Ile Leu Gly Gly Lys Asn Ser
                275                 280                 285

Gly Glu Gly Cys Val Ile Thr Arg Ser Arg Thr Ala Ala Leu Asp Ile
                290                 295                 300

Trp Asp Leu Asp Ile Lys Lys Gly Thr Trp Tyr Val Ile Glu Thr Asn
305                 310                 315                 320

Tyr Asp Arg Trp Lys Pro Pro Leu Val Leu Asp Asn Arg Arg Thr Pro
                325                 330                 335

Ala Met Lys Cys Leu Asn Gln Thr Ser Gln Glu Asn Ile Ser Leu Pro
                340                 345                 350

Thr Ile Tyr Asp Val Leu Ser Thr Lys Pro Val Leu Asn Lys Leu Thr
                355                 360                 365

Val Cys Thr Thr Leu Met Glu Val Asp Lys Gly His Thr Glu Thr Tyr
            370                 375                 380

Leu Arg Glu Cys Pro Asp Pro Cys Ser Pro Trp
385                 390                 395

<210> SEQ ID NO 4
<211> LENGTH: 395
<212> TYPE: PRT
<213> ORGANISM: Pan troglodytes
<220> FEATURE:
<223> OTHER INFORMATION: acid ceramidase

<400> SEQUENCE: 4

Met Pro Gly Arg Ser Arg Val Ala Leu Val Leu Leu Ala Ala Ala Val
1               5                   10                  15

Ser Cys Ala Val Ala Gln His Ala Pro Pro Trp Thr Glu Asp Cys Arg
                20                  25                  30

Lys Ser Thr Tyr Pro Pro Ser Gly Pro Thr Tyr Arg Gly Pro Val Pro
                35                  40                  45

Trp Tyr Thr Ile Asn Leu Asp Leu Pro Pro Tyr Lys Arg Trp His Glu
```

```
              50                  55                  60
Leu Met Leu Asp Lys Ala Pro Met Leu Lys Val Ile Val Asn Ser Leu
 65                  70                  75                  80

Lys Asn Met Ile Asn Thr Phe Val Pro Ser Gly Lys Ile Val Gln Val
                 85                  90                  95

Val Asp Glu Lys Leu Pro Gly Leu Leu Gly Asn Phe Pro Gly Pro Phe
            100                 105                 110

Glu Glu Glu Met Lys Gly Ile Ala Ala Val Thr Asp Ile Pro Leu Gly
            115                 120                 125

Glu Ile Ile Ser Phe Asn Ile Phe Tyr Glu Leu Phe Thr Ile Cys Thr
            130                 135                 140

Ser Ile Val Ala Glu Asp Lys Lys Gly His Leu Ile His Gly Arg Asn
145                 150                 155                 160

Met Asp Phe Gly Val Phe Leu Gly Trp Asn Ile Asn Asn Asp Thr Trp
                165                 170                 175

Val Ile Thr Glu Gln Leu Lys Pro Leu Thr Val Asn Leu Asp Phe Gln
            180                 185                 190

Arg Asn Asn Lys Thr Val Phe Lys Ala Ser Ser Phe Ala Gly Tyr Val
            195                 200                 205

Gly Met Leu Thr Gly Phe Lys Pro Gly Leu Phe Ser Leu Ser Leu Asn
            210                 215                 220

Glu Arg Phe Ser Ile Asn Gly Gly Tyr Leu Gly Ile Leu Glu Trp Ile
225                 230                 235                 240

Leu Gly Lys Lys Asp Ala Met Trp Ile Gly Phe Leu Thr Arg Thr Val
                245                 250                 255

Leu Glu Asn Ser Thr Ser Tyr Glu Glu Ala Lys Asn Leu Leu Thr Lys
            260                 265                 270

Thr Lys Ile Leu Ala Pro Ala Tyr Phe Ile Leu Gly Gly Asn Gln Ser
            275                 280                 285

Gly Glu Gly Cys Val Ile Thr Arg Asp Arg Lys Glu Ser Leu Asp Val
            290                 295                 300

Tyr Glu Leu Asp Ala Lys Gln Gly Arg Trp Tyr Val Val Gln Thr Asn
305                 310                 315                 320

Tyr Asp Arg Trp Lys His Pro Phe Phe Leu Asp Asp Arg Arg Thr Pro
                325                 330                 335

Ala Lys Met Cys Leu Asn Arg Thr Ser Gln Glu Asn Ile Ser Phe Glu
            340                 345                 350

Thr Met Tyr Asp Val Leu Ser Thr Lys Pro Val Leu Asn Lys Leu Thr
            355                 360                 365

Val Tyr Thr Thr Leu Ile Asp Val Thr Lys Gly Gln Phe Glu Thr Tyr
            370                 375                 380

Leu Arg Asp Cys Pro Asp Pro Cys Ile Gly Trp
385                 390                 395

<210> SEQ ID NO 5
<211> LENGTH: 393
<212> TYPE: PRT
<213> ORGANISM: Caenorhabditis elegans
<220> FEATURE:
<223> OTHER INFORMATION: acid ceramidase

<400> SEQUENCE: 5

Met Leu Arg Glu Leu Ser Val Leu Leu Val Ala Val Cys Ala Ala
 1               5                  10                  15

Lys His Val Glu Leu Pro Ala Pro Phe Lys Asp His Cys Ile Leu Asp
```

```
            20                  25                  30
Asp Lys Gln Asn Leu Tyr Asp Pro Ser Lys Gln Phe Asp Ile Lys Trp
            35                  40                  45

Tyr Asp Val Asn Leu Asp Leu Pro Pro Ser Glu Arg Trp Val Gln Ile
50                  55                  60

Ala Thr Ala Asn Lys Glu His Ile Ala Asp Leu Ile Gly Val Leu Ile
65                  70                  75                  80

Asn Leu Ile Thr Pro Trp Phe Pro Asn Ala Ile Asp Phe Val Asp Asp
                85                  90                  95

Val Phe Gly Asp Leu Ala Pro Lys Leu Ala Gln Pro Tyr Arg Asp Glu
                100                 105                 110

Ile Phe Ser Ile Ala Asn Ala Thr Gly Ile Pro Leu Gly Gln Ile Thr
                115                 120                 125

Met Tyr Asn Ile Phe Tyr Glu Ile Phe Thr Val Cys Thr Ser Val Ile
                130                 135                 140

Ala Gln Asp Lys Asp Gly His Val Phe His Ala Arg Asn Leu Asp Phe
145                 150                 155                 160

Gly Leu Phe Met Gly Trp Asp Pro Val Leu His Asp Trp Gln Ile Ser
                165                 170                 175

Gln Lys Leu Arg Lys Met Ile Ile Asn Val Asn Trp Leu Lys Asp Gly
                180                 185                 190

Lys Leu Leu Tyr Lys Ser Asn Asn Phe Ala Gly Tyr Ile Gly Ile Tyr
                195                 200                 205

Asn Gly Leu Lys Pro Asn Ala Phe Ser Leu Thr Ala Asp Asp Arg Phe
                210                 215                 220

Gln Leu Val Gly Gly Tyr Tyr Gly Ile Leu Lys Trp Val Phe Gly Leu
225                 230                 235                 240

Glu Ala Asp Gly Lys Trp Met Ser Trp Leu Ala Arg Glu Thr Leu Glu
                245                 250                 255

Thr Lys Thr Thr Tyr Leu Asp Ala Lys Glu His Leu Met Asn Thr Pro
                260                 265                 270

Met Leu Ser Pro Val Tyr Phe Ile Leu Gly Gly Ser Lys Lys Asp Glu
                275                 280                 285

Gly Cys Ile Ile Ala Arg Ser Leu Asp Lys Thr Ala Leu Leu Thr Glu
                290                 295                 300

Met Ala Thr Ser Pro His Gly Trp Tyr Leu Leu Glu Thr Asn Tyr Asp
305                 310                 315                 320

Gln Gly Thr Glu Asp Leu Tyr Leu Asp Asp Arg Asp Thr Pro Gly Phe
                325                 330                 335

Arg Cys Met Asp Lys Leu Thr Gln Lys Asn Val Gly Phe Glu Gly Ile
                340                 345                 350

Phe Asn Val Leu Ser Ser Arg Thr Asn Leu Asn Lys Leu Thr Thr Tyr
                355                 360                 365

Thr Val Leu Met Ser Val Glu Thr Ser Arg Phe Glu Thr Ile Leu Gln
                370                 375                 380

Ser Cys Pro Gly Glu Cys Tyr Pro Trp
385                 390

<210> SEQ ID NO 6
<211> LENGTH: 390
<212> TYPE: PRT
<213> ORGANISM: Danio rerio
<220> FEATURE:
<223> OTHER INFORMATION: acid ceramidase
```

<400> SEQUENCE: 6

```
Met Lys Leu Val Phe Arg Tyr Asn Ala Leu Phe Ile Ser Ile Phe Ile
1               5                   10                  15

His Ala Leu Tyr Val Gln Gly Leu Glu Asp Cys Arg Ser Gly Met Tyr
            20                  25                  30

Pro Pro Lys Gly Pro Thr Tyr Arg Gly Asn Val Thr Arg Tyr Thr Val
        35                  40                  45

Asn Leu Asp Leu Pro Pro Ser Glu Arg Trp Thr Gln Ile Ile Lys Asp
    50                  55                  60

Lys Asn Thr Glu Leu Ile Glu Met Val Gln Thr Ile Lys Asp Met Ala
65                  70                  75                  80

Lys Gly Phe Phe His Gly Lys Leu Val Asn Phe Val Asp Lys Glu Leu
                85                  90                  95

Pro Phe Ile Val Asp Thr Leu Pro Asn Pro Phe Asn Glu Glu Ile Lys
            100                 105                 110

Gly Ile Ala Ala Val Ser Gly Ile Pro Leu Gly Glu Ile Ala Leu Phe
        115                 120                 125

Asn Ile Phe Tyr Glu Val Phe Thr Val Cys Thr Ser Leu Val Ala Glu
    130                 135                 140

Asp Asn Asn Gly Asn Ile Tyr His Gly Arg Asn Leu Asp Phe Gly Leu
145                 150                 155                 160

Phe Met Gly Trp Asp Arg Gln Asn Lys Thr Trp Thr Leu Thr Glu Lys
                165                 170                 175

Leu Lys Pro Leu Val Val Asn Ile Asn Phe Glu Arg Lys Asn Gln Thr
            180                 185                 190

Val Phe Lys Ser Thr Ser Phe Ala Gly Tyr Val Gly Met Leu Thr Gly
        195                 200                 205

Ile Arg Pro Gly Glu Leu Thr Leu Thr Met Asn Glu Arg Phe Asp Phe
    210                 215                 220

Asp Gly Gly Tyr Ile Gly Ile Leu Asp Trp Ile Phe Gly Asn Arg Asp
225                 230                 235                 240

Gly Met Trp Thr Gly Phe Leu Thr Arg Arg Val Leu Glu Asn Ser Thr
                245                 250                 255

Ser Tyr Glu Asp Ala Lys Asp Gln Leu Ser Gln Thr Lys Leu Leu Ala
            260                 265                 270

Pro Val Tyr Phe Ile Leu Gly Gly Asn Arg Thr Gly Gln Gly Cys Val
        275                 280                 285

Ile Thr Arg Thr Arg Ile Asn Thr Leu Asp Ile Trp Glu Leu Glu Leu
    290                 295                 300

Met Leu Gly Arg Trp Tyr Val Leu Glu Thr Asn Tyr Asp His Trp Asp
305                 310                 315                 320

Lys Pro Met Phe Leu Asp Asp Arg Arg Thr Pro Ala Met Lys Cys Met
                325                 330                 335

Asn Gln Thr Thr Gln Ala Asn Ile Ser Leu Ala Ser Ile Tyr Asn Val
            340                 345                 350

Leu Ser Thr Lys Pro Val Leu Asn Lys Leu Thr Thr Tyr Thr Ser Leu
        355                 360                 365

Met Ala Val Ser Thr Gly Thr Leu Glu Ser Tyr Val Arg Asp Cys Pro
    370                 375                 380

Asn Pro Cys Thr Pro Trp
385                 390
```

<210> SEQ ID NO 7

<211> LENGTH: 394
<212> TYPE: PRT
<213> ORGANISM: Rattus norvegicus
<220> FEATURE:
<223> OTHER INFORMATION: acid ceramidase

<400> SEQUENCE: 7

```
Met Leu Gly Arg Ser Leu Leu Thr Trp Val Leu Ala Ala Ala Val Thr
1               5                   10                  15

Cys Ala Gln Ala Gln Gln Val Pro Pro Trp Thr Glu Asp Cys Arg Lys
            20                  25                  30

Ser Thr Tyr Pro Pro Ser Gly Pro Thr Tyr Arg Gly Pro Val Pro Trp
        35                  40                  45

Tyr Thr Ile Asn Leu Asp Leu Pro Pro Tyr Lys Arg Trp His Glu Leu
    50                  55                  60

Leu Ala His Lys Ala Pro Val Leu Arg Thr Leu Val Asn Ser Ile Ser
65                  70                  75                  80

Asn Leu Val Asn Ala Phe Val Pro Ser Gly Lys Ile Met Gln Met Val
                85                  90                  95

Asp Glu Lys Leu Pro Gly Leu Ile Gly Ser Ile Pro Gly Pro Phe Gly
            100                 105                 110

Glu Glu Met Arg Gly Ile Ala Asp Val Thr Gly Ile Pro Leu Gly Glu
        115                 120                 125

Ile Ile Ser Phe Asn Ile Phe Tyr Glu Leu Phe Thr Met Cys Thr Ser
    130                 135                 140

Ile Ile Thr Glu Asp Gly Lys Gly His Leu His Gly Arg Asn Met
145                 150                 155                 160

Asp Phe Gly Ile Phe Leu Gly Trp Asn Ile Asn Asn Thr Trp Val
                165                 170                 175

Val Thr Glu Glu Leu Lys Pro Leu Thr Val Asn Leu Asp Phe Gln Arg
            180                 185                 190

Asn Asn Lys Thr Val Phe Lys Ala Thr Ser Phe Ala Gly Tyr Val Gly
        195                 200                 205

Met Leu Thr Gly Phe Lys Pro Gly Leu Leu Ser Leu Thr Leu Asn Glu
    210                 215                 220

Arg Phe Ser Leu Asn Gly Gly Tyr Leu Gly Ile Leu Glu Trp Met Phe
225                 230                 235                 240

Gly Lys Lys Asn Ala Gln Trp Val Gly Phe Ile Thr Arg Ser Val Leu
                245                 250                 255

Glu Asn Ser Thr Ser Tyr Glu Glu Ala Lys Asn Ile Leu Thr Lys Thr
            260                 265                 270

Lys Ile Thr Ala Pro Ala Tyr Phe Ile Leu Gly Gly Asn Gln Ser Gly
        275                 280                 285

Glu Gly Cys Val Ile Thr Arg Glu Arg Lys Glu Ser Leu Asp Val Tyr
    290                 295                 300

Glu Leu Asp Pro Lys His Gly Arg Trp Tyr Val Val Gln Thr Asn Tyr
305                 310                 315                 320

Asp Arg Trp Lys Asn Thr Leu Phe Leu Asp Asp Arg Arg Thr Pro Ala
                325                 330                 335

Lys Lys Cys Leu Asn His Thr Thr Gln Lys Asn Leu Ser Phe Ala Thr
            340                 345                 350

Ile Tyr Asp Val Leu Ser Thr Lys Pro Val Leu Asn Lys Leu Thr Val
        355                 360                 365

Phe Thr Thr Leu Ile Asp Val Thr Lys Asp Gln Phe Glu Ser His Leu
    370                 375                 380
```

```
Arg Asp Cys Pro Asp Pro Cys Ile Gly Trp
385                 390
```